US007531626B2

(12) United States Patent
Graham et al.

(10) Patent No.: US 7,531,626 B2
(45) Date of Patent: May 12, 2009

(54) TENEBRIO ANTIFREEZE PROTEINS

(75) Inventors: Laurie A. Graham, Kingston (CA); Yih-Cherng Liou, Kingston (CA); Virginia K. Walker, Sydenham (CA); Peter L. Davies, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 209 days.

(21) Appl. No.: 10/861,858

(22) Filed: Jun. 4, 2004

(65) Prior Publication Data
US 2006/0116506 A1 Jun. 1, 2006

Related U.S. Application Data

(62) Division of application No. 10/032,658, filed on Nov. 8, 2001, now Pat. No. 6,747,130, which is a division of application No. 08/882,907, filed on Jun. 26, 1997, now Pat. No. 6,392,024.

(51) Int. Cl.
*C07K 14/00* (2006.01)
*C07H 21/00* (2006.01)
*C12P 21/00* (2006.01)
*C12N 5/10* (2006.01)
*C12N 1/21* (2006.01)
*C12N 1/15* (2006.01)
*C12N 5/06* (2006.01)
*C12N 1/16* (2006.01)

(52) U.S. Cl. .......... 530/350; 435/69.1; 435/325; 435/410; 435/252.3; 435/254.11; 435/255.1; 435/348; 435/252.1; 536/23.1

(58) Field of Classification Search ............ 530/350, 530/252.3, 254.1, 255.1, 325, 348, 410, 69.1; 536/23.1; 435/254.23, 254.2, 69.1, 325, 435/410, 252.1, 254.11, 255.1, 348, 252.3
See application file for complete search history.

(56) References Cited

U.S. PATENT DOCUMENTS

| | | | |
|---|---|---|---|
| 5,118,792 A | 6/1992 | Warren et al. | |
| 5,139,950 A | 8/1992 | Klaenhammer et al. | |
| 5,296,462 A | 3/1994 | Thomashow | |
| 5,356,816 A | 10/1994 | Thomashow | |
| 5,358,931 A | 10/1994 | Rubinsky et al. | |
| 5,627,051 A | 5/1997 | Duman | |
| 5,633,451 A | 5/1997 | Duman | |

FOREIGN PATENT DOCUMENTS

WO    WO 96/40973 A1    12/1996

OTHER PUBLICATIONS

Branden et al., Introduction to Protein Structure, Garland Publishing Inc., New York, p. 247, 1991.*
Witkowski et al., Biochemistry 38:11643-11650, 1999.*
Chakrabarty, A., et al., "The effect of enhanced α-helicity on the activity of a winter founder antifreeze polypeptide," *Eur. J. Biochem*, 202:1057-1065 (1991).
Chao, H., et al., "Structure-function relationship in the globular type III antifreeze protein: Identification of a cluster of surface residues required for binding to ice," *Protein Science*, 3:1760-1769 (1994).
Davies, P. L., et al., "Biochemistry of fish antifreeze proteins," *FASEB J.*, 4:2460-2468 (1990).
DeVries, A. L. , "Antifreeze Peptides and Glycopeptides inCold-Water Fishes," *Annu. Rev. Physiol.*, 45:245-260 (1983).
Duman, J., et al., "The role of Hemolymph Proteins in the Cold Tolerance of Insects," *Ann. Rev. Phsiol.*, 45:261-270 (1983).
Fourney, R. M., et al., "Heterogeneity of antifreeze polypeptides from the Newfoundland winter flounder, *Pseudopleuronectes americanus*," *Can. J. Zool.*, 62:28-33 (1984).
Graham, L. A., et al., "Cloning and Baculovirus Expression of a Desiccation Stress Gene from the Beetle, *Tenebrio molitor*," *Insect Biochem. Molec. Biol.*, 26(2):127-133 (1996).
Graham, L. A., et al., "Hyperactive antifreeze protein from beetles," *Nature*, 388:727-728 (1997).
Grimstone, A. V., et al., "Further Studies on the Rectal Complex of the Mealworm *Tenebrio molitor*, L. (*coleoptera, Tenebrionidae*)," *Philos. Trans.*, 253(B):343-382 (1968).
Hew, C. L., et al., "Presence of cystine-containing antifreeze proteins in the spruce budworm, *Choristoneura fumiferana*," *Can. J. Zool.*, 61:2324-2328 (1983).
Horwath, K. L., et al., "Tracking the profile of a specific antifreeze protein and its contribution to the thermal hysteresis activity in cold hardy insects," *Eur. J. Entomol.*, 93:419-433 (1996).
Li, X., et al., "Structure of an Antifreeze Polypeptide and Its Precursor from the Ocean Pout, *Macrozoarces americanus*," *J. Biol. Chem.*, 260(24):12904-12902 (1985).
Ng, N. F., et al., "Structure of an Antifreeze Polypeptide Precursor from the Sea Raven, *Hemitripterus americanus*," *J. Biol. Chem.*, 261(33):15690-15695 (1986).
Ochman, H., et al., "Genetic Applications of an Inverse Polymerase Chain Reaction," *Genetics*, 120:621-523 (1988).
Peterson, J. L., et al., "Composition of a Protein Antifreeze from Larvae of the Beetle," *J. Exp. Zool.*, 210(2):361-367 (1979).

(Continued)

*Primary Examiner*—Delia M Ramirez
(74) *Attorney, Agent, or Firm*—Licata & Tyrrell P.C.

(57) ABSTRACT

A novel class of thermal hysteresis (antifreeze) proteins (THP) that have up to 100 times the specific activity of fish antifreeze proteins has been isolated and purified from the mealworm beetle, *Tenebrio molitor*. Internal sequencing of the proteins, leading to cDNA cloning and production of the protein in bacteria has confirmed the identity and activity of the 8.4 to 10.7 kDa THP. They are novel Thr- and Cys-rich proteins composed largely of 12-amino-acid repeats of cys-thr-xaa-ser-xaa-xaa-cys-xaa-xaa-ala-xaa-thr. At a concentration of 55 µg/mL, the THP depressed the freezing point 1.6° C. below the melting point, and at a concentration of ~1 mg/mL the THP or its variants can account for the 5.5° C. of thermal hysteresis found in *Tenebrio* larvae. The THP function by an adsorption-inhibition mechanism and produce oval-shaped ice crystals with curved prism faces.

19 Claims, 7 Drawing Sheets

OTHER PUBLICATIONS

Paterson, J. L., et al., "Purification and Composition of Protein Antifreezes with High Cysteine Contents from Larvae of the Beetle, *Tenebrio molitor*," *J. Exp. Zool.*, 219:381-384 (1982).

Rubin, G. M., et al., "Vectors for P element-mediated gene transfer in *Drosophila*," *Nucl. Acids Res.*, 11(18):6341-6351 (1983).

Rubin, G. M., et al., "Genetic Transformation of *Drosophila* with Transposable Element Vectors," *Science*, 218:348-353 (1982).

Saikl, R. K., et al., "Enzymatic Amplification of β-Globin Genomic Sequences and Restriction Site Analysis for Diagnosis of Sickle Cell Anemia," *Science*, 230:1350-1354 (1985).

Schneppenheim, R., et al., "Isolation and Characterization of Freezing-Point Depressing Peptides from Larvae of *Tenebrio molitor*," *Comp. Biochem. Physiol.*, 67B:561-568 (1980).

Sönnichsen, F.D., et al., "Comparative modeling of the three-dimensional structure of Type II antifreeze protein," *Protein Sci.*, 4:460-471 (1995).

Tang, W., et al., "Studies of Structure-Function Relationship of Insect Antifreeze Proteins," Abstract, American Society for Biochemistry and Molecular Biology Conference, Washington, D.C. 547 (May 21-25, 1994).

Tomchaney, A. P., et al., "Purification, Composition, and Physical Properties of a Thermal Hysteresis 'Antifreeze' Protein from Larvae of the Beetle, *Tenebrio molitor*," *Biochemistry*, 21:716-721 (1982).

Wen, D., et al., "Structure-Function Relationships in an Antifreeze Polypeptide," *J. Biol. Chem.*, 267(20):14102-14108 (1992).

Tschoop, J. F., et al., "Heterologous Gene Expression in Methylotrophic Yeast," *Biotechnology*, 18:308-322 (1991).

Bork, P., "Powers and Pitfalls in Sequence Analysis:The 70% Hurdle", Genome Research 2000 10:398-400.

Broun et al., "Catalytic Plasticity of Fatty Acid Modification Enzymes Underlying Chemical Diversity of Plant Lipids", Science 1998 282:1315-1317.

Seffernick et al., "Melamine Deaminase and Atrazine Chlorohydrolase:98 Percent Identical but Functionally Different", J. Bacteriology 2001 183 (8) :2405-2410.

van de Loo et al., "An oleate 12-hydroxylase from *Ricinus communis* L. is a fatty acyl desaturase homolog", Proc. Natl. Acad. Sci. USA 1995 92:6743-6747.

\* cited by examiner

Figure 6 (1/3)

```
YL-1   TAAACAGCGAGATAAACAACAATACTACATAAAACTATGGCGTTCAAAACGTGTGGTTTTTC
YL-2               AAACAATATTACAAAAAACTATGGCATTCAAAACGTGTGGTTTTTC
YL-4                   CAAAAAAGTATGTCATTCAAAATAAGTACTTTTAC
YL-3               AAACAACAATATTACAAAAAACTATGGCATTCAAAACGTGTGGTTTTTC
5-15   AAACAGCGAGATAAACAACAATATTACAAAAAACTATGGCATTCAAAACGTGTGGTTTTTC
       ************** ******* **** **** **** * *******   **  **** *

YL-1                                               M  A  F  K  T  C  G  F  S
YL-2                                               .  .  .  .  .  .  .  .  .
YL-4       5' UNTRANSLATED REGION                  .  S  .  .  I  S  T  .  T
YL-3                                               .  .  .  .  .  .  .  .  .
5-15                                               .  .  .  .  .  .  .  .  .

YL-1   AAAAAAATGGTTAGTAATAGCAGTTATAGTTATGTGTTTGTGTACCGAGTGTTATTGCCAC
YL-2   AAAAAAATGGTTAGTAATAGCAGTTATAGTTATGTGTTTGTGTACCGAGTGTTATTGCCAA
YL-4   AAAAATCTGGTTAATTATAGCAGTTATCGTTATGTGTTTGTGTAACGAGTATAATTGCCAG
YL-3   AAAAAAATGGTTAATAATAGCAGTTATAGTTATGTGTTTGTGTACCGAGTGTTATTGCCAG
5-15   AAAAAAATGGTTAATAATAGCAGTTATAGTTATGTGTTTGTGTACCGAGTGTTATTGCCAA
       *****  ******  * *********** ******************* *****  * *******

YL-1    K  K  W  L  V  I  A  V  I  V  M  C  L  C  T  E  C  Y  C  H
YL-2    .  .  .  .  .  .  .  .  .  .  .  .  .  .  ..  .  .  .  .  Q
YL-4    .  I  .  .  I  .  .  .  .  .  .  .  .  .  N  .  Y  N  .  Q
YL-3    .  .  .  .  I  .  .  .  .  .  .  .  .  .  .  .  .  .  .  Q
5-15    .  .  .  .  I  .  .  .  .  .  .  .  .  .  .  .  .  .  .  Q

YL-1   TGCACTGGGGGTGCTGATTGTACTAGTTGTACAGATGCATGCACTGGTTGTGGAAATTGTC
YL-2   TGCACTGGGGGTGCTGATTGCACTAGTTGTACAGGAGCATGCACTGGTTGTGGAAACTGTC
YL-4   TGCACTGGGGCTGCTGATTGTACTAGTTGTACAGCAGCATGCACTGGTTGTGGAAACTGTC
YL-3   TGCACTGGGGGTGCTGATTGTACTAGTTGTACAGCAGCATGCACTGGTTGTGGAAGTTGTC
5-15   TGCACTGGGGGTGCTGATTGTACTAGTTGTACAGCAGCATGCACTGGTTGTGGAAGTTGTC
       **********  ********* ************    *********************  ****

YL-1    C  T  G  G  A  D  C  T  S  C  T  D  A  C  T  G  C  G  N  C
YL-2    .  .  .  .  .  .  .  .  .  .  .  G  .  .  .  .  .  .  .  .
YL-4    .  .  .  A  .  .  .  .  .  .  .  A  .  .  .  .  .  .  .  .
YL-3    .  .  .  .  .  .  .  .  .  .  .  A  .  .  .  .  .  .  S  .
5-15    .  .  .  .  .  .  .  .  .  .  .  A  .  .  .  .  .  .  S  .

YL-1   CAAATGCACATACGTGTACCGATTCCAAAAATTGTGTCAAGGCAGCA---------------
YL-2   CAAATGCAGTAACGTGTACCAATTCTCAACATTGTGTCAAGGCAAAT---------------
YL-4   CAAATGCAATAACGTGTACCGGTTCTAAAAATTGTGTCAGGGCAACA---------------
YL-3   CAAATGCGCATACGTGTACCGATTCTAAAAATTGTGTCAGGGCAGAAACGTGTACCGATTC
5-15   CAAATGCGCATACGTGTATCGATTCTAAAAATTGTGTCAGGGCAGAAACGTGTACCGATTC
       *******  ******* *  *** *** ** *********  ****

```
YL-1   ----------------------ACATGTACTGGATCTACAAAATGTAATACCGCCAGGACG
YL-2   ----------------------ACATGTACTGGGTCTACAGATTGTAATACAGCCCAGACG
YL-4   ----------------------ACATGTACTGGGTCTACAAACTGTAATAGAGCCACGACG
YL-3   TGAAAATTGTGTCAAGGCACATACATGTACTGGATCTAGAAACTGTAATACAGCCATGACG
5-15   TGAAAATTGTGTCAAGGCACATACATGTACTGGATCTAGAAACTGTAATACAGCCATGACG
                             ***********  ****  *  *  *******  ***  ****
YL-1   -------------------  T  C  T  G  S  T  K  C  N  T  A  R  T
YL-2   -------------------  .  .  .  .  .  .  D  .  .  .  .  Q  .
YL-4   -------------------  .  .  .  .  .  .  N  .  .  R  .  T  .
YL-3   E  N  C  V  K  A  H  .  .  .  .  .  .  R  N  .  .  .  .  M  .
5-15   E  N  C  V  K  A  H  .  .  .  .  .  .  R  N  .  .  .  .  M  .

YL-1   TGTACAAACTCAAAAGACTGTTTTGAAGCCAAAACATGTACTG-----------------
YL-2   TGTACAAACTCAAAAGACTGTTTTGAAGCCAACACATGTACTG-----------------
YL-4   TGTACAAATTCAAAAGGCTGTTTAGAAGCCACAACATGTACTGGGTCTACACACTGTCATA
YL-3   TGTACAAACTCAAAAGACTGTTTTGAAGCCAAAACATGTACTG-----------------
5-15   TGTACAAACTCAAAAGACTGTTTTGAAGCCAAAACATGTACTG-----------------
       ********  *******  ******  *******    **********
YL-1   C  T  N  S  K  D  C  F  E  A  K  T  C  T  -----------------
YL-2   .  .  .  .  .  .  .  .  .  N  .  .  .  -----------------
YL-4   .  .  .  .  .  G  .  L  .  .  T  .  .  .  G  S  T  H  C  H
YL-3   .  .  .  .  .  .  .  .  .  .  .  .  .  .  -----------------
5-15   .  .  .  .  .  .  .  .  .  .  .  .  .  .  -----------------

YL-1   ------------------------------------------------------------
YL-2   ------------------------------------------------------------
YL-4   GAGCCACGACGTGTACAAATTCAAAAGACTGTTTTGAAGCCACAACATGTACTGGCTCAAG
YL-3   ------------------------------------------------------------
5-15   ------------------------------------------------------------

YL-1   ------------------------------------------------------------
YL-2   ------------------------------------------------------------
YL-4   R  A  T  T  C  T  N  S  K  D  C  F  E  A  T  T  C  T  G  S  S
YL-3   ------------------------------------------------------------
5-15   ------------------------------------------------------------

YL-1   ----------------------------ACTCAACCAACTGTTACAAAGCTACAGCCTGT
YL-2   ----------------------------ACTCAACCAACTGTTACAAAGCTACAGCCTGT
YL-4   CAACTGTTACACTGCTACAACATGTACTAACTCAACCAACTGTTACAAAGCTACAGCCTGT
YL-3   ----------------------------ACTCAACCAACTGTTACAAAGCTACAGCCTGT
5-15   ----------------------------ACTCAACCAACTGTTACAAAGCTACAGCCTGT
                                   ****************************
YL-1   -----------------------  D  S  T  N  C  Y  K  A  T  A  C
YL-2   -----------------------  .  .  .  .  .  .  .  .  .  .  .
YL-4   N  C  Y  T  A  T  T  C  T  N  .  .  .  .  .  .  .  .  .  .  .
YL-3   -----------------------  .  .  .  .  .  .  .  .  .  .  .
5-15   -----------------------  .  .  .  .  .  .  .  .  .  .  .
```

FIGURE 6 (3/3)

```
YL-1   ACCAATTCAACAGGATGTCCCGGACATTAAGTTTTTCTATTGTCAACAAT--AATAAAACA
YL-2   ACCAATTCATCAGGATGTCCCGGACATTAAGTTTTTCTATTGTCAACAAT--CATAAAACA
YL-4   ACCAATTCAACAGGATGTCCCGGACATTAGGTTTTTTTATTGTCAACAATAAAATAAAACA
YL-3   ACCAATTCAACAGGATGTCCCGGACATTAAGTTTTTCTATTGTCAACAAT--AATAAAACA
5-15   ACCAATTCAACAGGATGTCCCGGACATTAAGTTTTTCTATTGTCAACAAT--AATAAAACA
       ********  ******************  ******  *************   *******
YL-1    T   N   S   T   G   C   P   G   H   *
YL-2    .   .   .   S   .   .   .   .   .
YL-4    .   .   .   .   .   .   .   .   .            3' UNTRANSLATED REGION
YL-3    .   .   .   .   .   .   .   .   .
5-15    .   .   .   .   .   .   .   .   .

YL-1   CACTTACTGTTATCTTAGCTAAAACATAATTGTAAGC-TCACTCTGTTTTGTATCCTATCT
YL-2   CAATTATTGTTAGCTAAGTTAAAACT---CTGTA---------TTGTATCCGATC-----T
YL-4   AAACTGTTCTTATCTAAGCTAAAACATAAATGTAAACGTTAATTTGTATTCTATCCGATCT
YL-3   C-GGAGGGATAGTCTAAGCTAAAACATAATTGTAAGC-TTACTCTGTATTGTATCCGATCT
5-15   C-GGAGGGATAGTCTAAGCTAAAACATAATTGTAAGC-TTACTCTGTATTGTATCCGATCT
         *   ** ** ******    ****         *** *   ***        *

YL-1   GTCTCT--GCCTCCGAAGGATGATAATTTTGTACTGGGAGCGAAAGGTTTATCCGACAATA
YL-2   GTCTCTTTGCCTCCCAAGGATGATAATTTTGTACTGGGAGCGAAAGGGTTATCGGACAATA
YL-4   GTCCCTTTGCGCCCTAAGGA---TAATTTTGTACAGGGAGAGAAAGGCTATCGGACAATA
YL-3   GTCTCTTTGCCTCCCAAGGATGATAATTTTGTACTGGGAGCGAAAGGGTTATCCGACAATA
5-15   GTCTCTTTGCCTCCCAAGGATGATAATTTTGTACTGGGAĠCGAAAGGGTTACCGGACAATA
       *** **   **  ** *****   *********** *****  **** *   **  *   *******

YL-1   ATA-------AACTAAAATAATTGATATAAAAAAAAAAAAAAA
YL-2   ATA-------AACTAAAATAATTGATATAAAAAAAAAAAAAAA
YL-4   ATA-------AACATTGTTAATATACATAAAAAAAAAAAAAAA
YL-3   ATAATTAATAAACTAAA-TAATTG--ATAAAAAAAAAAAAAAA
5-15   ATAATTAATAAACTAAAATAATTGATATAAAAAAAAAAAAAAA
       ***       ***    ****    **
```

US 7,531,626 B2

TENEBRIO ANTIFREEZE PROTEINS

CROSS REFERENCE TO RELATED APPLICATIONS

This patent application is a divisional of U.S. patent application Ser. No. 10/032,658, filed Nov. 8, 2001, issued as U.S. Pat. No. 6,747,130, which is a divisional of U.S. patent application Ser. No. 08/882,907, filed Jun. 26, 1997, now issued as U.S. Pat. No. 6,392,024.

BACKGROUND OF THE INVENTION

In modern times, refrigeration and, particularly, freezing have become common and preferred means for storage of biological materials. While refrigeration preserves some important properties of the samples, others continue to deteriorate at a slow but significant rate. Frozen storage may arrest most of this deterioration, but the combination of freezing and thawing introduces other changes which destroy other important properties.

In the modern world, frozen foods have become a mainstay of the human diet. To ensure a high quality product, sufficient for the demanding consumer's palate, frozen vegetables in particular, and frozen desserts, such as ice cream, have been the subject of extensive research by food processors. It is now known that ice recrystallization can have a substantial negative impact on the taste and texture of frozen foods. The advent of frost-free freezers has exacerbated this situation, which has been more traditionally associated with temperature fluctuations during transportation. After a relatively short period of time at other than sub-zero temperatures or even at sustained freezing temperatures, many frozen foods become less desirable, or worse, totally unsuitable, for human consumption.

While a variety of techniques have been implemented to mitigate the damages associated with recrystallization, and limited success has been attained, significant problems remain. Often, modifications to the processing of the frozen foods drastically affect their quality, color, flavor, and/or texture. Moreover, the additional processing can be very expensive and time consuming, rendering the techniques uneconomical. Similar difficulties have been associated with incorporating additives to the foodstuffs.

For biologics, such as therapeutic drugs, blood plasma, mammalian cells for use in tissue culture, and the like, freezing can cause extensive damage. For example, the freezing process itself kills most eukaryotic cells, and cells subjected to even one freezing and thawing cycle exhibit greatly reduced viability. Impaired function of living cells is also prevalent in tissue cryopreservation, with concomitant drawbacks for organ transplants. Similarly, frost or other freezing damage to plants presents a serious problem in agriculture. Finally, drugs can become ineffective, or even dangerous, if not maintained under required strict temperature conditions.

Although the first description of protein-mediated thermal hysteresis (TH, as defined below) was noted in *Tenebrio molitor* hemolymph approximately 30 years ago (Grimstone, et al, *Philos. Trans.* B 253:343 (1968)), numerous attempts to purify these thermal hysteresis proteins (THP) failed to yield pure fractions with enough TH to account for the hemolymph activity (Grimstone, et al., (1968); Paterson & Duman, *J. Exp. Zool.* 210:361 (1979); Schneppenheim & Theede *Comp. Biochem. Physiol.* 67B:561 (1980); Tomchaney, et at, *Biochemistry* 21:716 (1982); Paterson & Duman *J. Exp. Zool.* 219:381 (1982); and (Horwath, et al., *Eur. J. Entomol.* 93: 419 (1996)). Homogeneity of these proteins was not proven, and they differed in amino acid composition from each other and from the compositions reported here.

There exists a need for new techniques and compositions suitable for improving the preservation characteristics of organic materials at low temperatures, including storage of frozen foods and the viability of biologics. Ideally, these techniques and compositions will be inexpensive, yet completely safe and suitable for human consumption or in vivo therapeutic uses. There also exists a need for new techniques and compositions suitable for depressing the freezing point or inhibiting freezing in non-organic systems, such as in deicing treatments. The present invention fulfills these and other needs.

SUMMARY OF THE INVENTION

The common yellow mealworm beetle, *Tenebrio molitor*, is a freeze-tolerant pest of stored grains in temperate regions. Larvae are able to supercool to an average temperature of −12° C. (Johnston & Lee, *Cryobiol.* 27:562 (1990)). A second line of defense against freezing is the thermal hysteresis (TH) activity of their hemolymph, which allows the insects to depress their freezing points in the presence of ice or ice nucleators. This activity is quantified as the temperature difference (° C.) between the freezing and melting points of a solution containing ice. Values for TH in *Tenebrio* hemolymph range from 1 to 10° C. according to the method of measurement and the conditions under which the insects are reared (Hansen & Baust, *Biochim. Biophys. Acta* 957:217 (1988); and Patterson & Duman, *J. Exp. Biol.* 74:37 (1978)).

This invention provides for the nucleic acid molecules that encode the proteins responsible for the thermal hysteresis in *Tenebrio* larvae. Nucleic acid sequencing predicts a thermal hysteresis protein (THP) having at least greater than one repeat of a 12 contiguous amino acid motif. This repeating motif is rich in cysteine and threonine (SEQ ID NO:1). In addition to the repeating motif, the N-terminus of the class of THP of this invention is a 16 amino acid motif (SEQ ID NO:3)

In another embodiment, this invention provides for the recombinant proteins derived from the nucleic acids of this invention. The protein is characterized as having a calculated molecular weight of between 7 and 13 kDa, a pI of about 8 to 10 and a TH activity of greater than about 1.5° C. at 1 mg protein/mL.

The invention also provides for antibodies raised against the proteins of this invention and antibodies that bind to the proteins of this invention. The invention provides for antibodies specifically immunoreactive under immunologically reactive conditions to an antifreeze protein comprising SEQ ID NO: 4. The invention also provides for an antibody, specifically immunoreactive under immunologically reactive conditions, to an antifreeze protein comprising the protein encoded by the nucleic acid of claim 1.

In a further embodiment of this invention, transformed yeast, bacteria and other transgenic organisms are provided for. Many frozen foodstuffs suffer from formation of ice crystals due to sustained subfreezing temperatures or repeated freeze-thaw cycles. The presence of the THP of this invention will provide for a longer shelf-life, making these foodstuffs more palatable. Transgenic animals and plants are envisioned as better surviving sub-freezing temperatures.

The invention provides for an organism into which, or into an ancestor thereof, an exogenous nucleic acid sequence which specifically hybridizes under stringent conditions to SEQ ID NO: 2 or 5 or the nucleic acid of claim 1 has been introduced, and the organism translates the exogenous nucleic acid into an antifreeze protein. Also provided for is an organism with an exogenous nucleic acid sequence which is translated into an antifreeze protein that is expressed externally from the organism. In a preferred embodiment, the organism is a fish. In further preferred embodiments, the organism is a fish is kept in a salt-water environment, or, the fish is a member of the family Salmonidae. In other preferred embodiments, the organism can be a plant, a fungus, a yeast or a bacteria. In another embodiment, if the organism is a yeast, it can be selected from the group consisting of *Torulopsis holmil, Saccharomyces fragilis, Saccharomyces cerevisiae, Saccharomyces lactis,* and *Candida pseudotropicalis.* In another embodiment, if the organism is a bacterium, it can be selected from the group consisting of *Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacterin breve,* and *Bifidobacterium longum.* Plants transformed with THP sequences can include grapes, oilseed plants such as canola, grains, citrus and sugar cane.

The invention provides for a method for decreasing the freezing point of an aqueous solution involving the addition of an antifreeze protein to the aqueous solution. In a preferred embodiment, the method involves the addition of the antifreeze protein encoded by the nucleic acid of claim 1 to the aqueous solution. In other preferred embodiments, the aqueous solution is applied to an organism; the antifreeze protein is produced by recombinant means; the antifreeze protein can specifically bind to the antibody of claim 13 or claim 14; the antifreeze protein is selected from the group consisting of YL-1, YL-2, YL-3 and YL-4; and/or, the antifreeze protein is encoded by a nucleic acid molecule which specifically hybridizes to the nucleic acid of SEQ ID NO:2 or 5.

In addition, it is contemplated that the addition of the THP of this invention to aqueous solutions may better preserve organs and other biologicals in transit.

A further understanding of the nature and advantages of the present invention may be realized by reference to the remaining portions of the specification, the figures and claims.

BRIEF DESCRIPTION OF THE FIGURES

FIG. 6 is an alignment chart of recombinant isoforms of THP (YL-1 (SEQ ID NO:10), YL-2 (SEQ ID NO:12), YL-4 (SEQ ID NO:14), YL3 (SEQ ID NO:16) and 5-15 (SEQ ID NO:18)). The positions in which the nucleotide is conserved in all cDNA sequences (consensus sequence = SEQ ID NO:20) are marked by an asterisk (*). The complete amino acid sequence is indicated for YL-1 (SEQ ID NO:11). Residues of other isoforms (YL-2 (SEQ ID NO:13), YL-4 (SEQ ID NO:15), YL3 (SEQ ID NO:17) and 5-15 (SEQ ID NO:19)) which are identical to those found in YL-1 are indicated by a period (.). Differences are shown by bold face type where found. Gaps in both the cDNA and protein sequences are indicated by dashes (------).

DETAILED DESCRIPTION OF THE INVENTION

Figure 1:
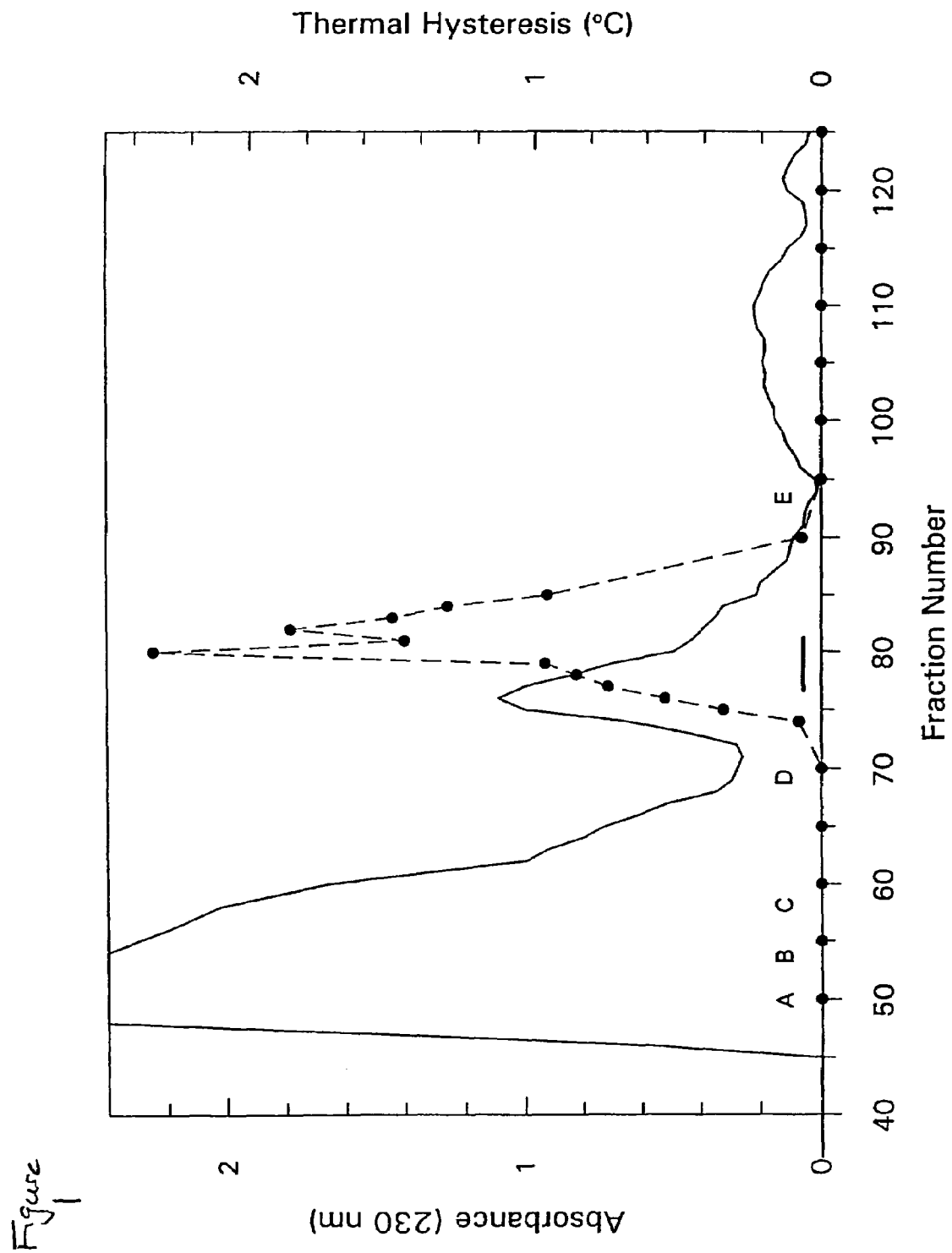
FIG. 1 is a chromatogram of diluted *Tenebrio* hemolymph loaded onto an S-100 SEPHACRYL® (Pharmacia) column (92 cm×1.6 cm) and eluted with hemolymph buffer without phenylthiocarbamide (see text).

This invention relates to isolated nucleic acid sequences encoding a novel class of antifreeze protein (THP). The procedure for obtaining natural THP genes generally involves constructing or obtaining a gene library from *Tenebrio molitor*, detecting and isolating the desired gene, cloning it, and expressing it in a suitable host cell and then purifying the expressed protein. The natural protein can be used without modification or it can be modified in a variety of ways without affecting its TH activity.

The amino acid compositions of the purified proteins and the deduced mature sequences are very similar. The THPs are particularly rich in Cys (18-19%) and Thr (20-26%) and deficient in several hydrophobic amino acids, notably Leu and Ile. The overall hydrophilicity is approximately 55% (Wishard, et al., *Comput. Appl. Biosci.* 10:121 (1994)), which is much higher than that found in fish antifreeze proteins (AFPs) (Sonnichsen, et al., *Prot. Sci.* 4:460 (1995)).

The primary structure of the mature THP is very unusual (FIG. 4) and is not similar to any other known sequence. The first 20 amino acids contains 6 Cys spaced at irregular intervals ($Cx_5Cx_2Cx_3Cx_2Cx_2C$; SEQ ID NO:22), and this sequence overlaps with the first of a series of 12-amino-acid repeats that continue until the end of the protein. Cys is repeated at 6-residue intervals throughout this region, which has the consensus sequence CTxSxxCxxAxt (SEQ ID NO:1). The N-terminal Cys spacing has some elements in common with zinc-binding motifs (Klug & Schwabe, *FASEB J.* 9:597 (1995)). However, extensive dialysis against 10 mM EDTA or 10 mM phenanthroline, and the subsequent addition of 2 mM $ZnCl_2$ (or 2 mM $CaCl_2$) to chelator-free preparations incubated for 1 h at 22° C. does not affect activity, suggesting that there is no role for divalent metal ions in TH activity. At least some of the Cys residues are involved in disulfide bridges because all activity is lost on incubation with 10 mM dithiothreitol at 37° C. for 20 min, whereas no activity is lost under the same conditions in the absence of reducing agent. There is no effect of N-ethylmaleimide on TH activity, which suggests that if free Cys are present they can be modified without loss of activity.

The differences in length between the THP variants represent multiples of the 12-amino-acid repeat, suggesting that each repeat may form a functional domain. Although the THP repeats are short, they may fold independently to form a chain, which could explain the discrepancy between the actual and apparent molecular weights (see, infra) of the proteins as being due to asymmetry.

There is no structural similarity between *Tenebrio* THPs and fish AFPs. Fish type II AFP, which contains 10 Cys, does not display any repetitive structure or regularity in Cys spacing. Fish type I AFP and the antifreeze glycoprotein are built up of repetitive elements, but neither contains Cys (Davies & Hew, *FASEB J.* 4:2460 (1990)). It is, however, intriguing that the most abundant residue in *Tenebrio* THPs, Thr, is also the amino acid thought to play a central role in binding fish AFPs types I and III to the ice surface (Wen & Laursen *J. Biol. Chem.* 267:14102 (1992); and Chao. et al., *Prot. Sci.* 3:1760 (1994)).

However, like fish antifreeze proteins, *Tenebrio* THP appears to act by an adsorption-inhibition mechanism. Ice crystals in the presence of sufficient THP to produce about 1° C. of thermal hysteresis, stop growing until the non-equilibrium freezing point is exceeded. At that point, ice crystals burst forth from the crystal nucleator to form a solid mass of ice along the a-axis. At low thermal hysteresis activities, the ice fronts are broad and smooth. However, at high thermal hysteresis values, the ice fronts are no longer smooth. In contrast, once the freezing point is exceeded in the presence of fish AFPs, myriad ice spicules burst out along and parallel to the c-axis.

In addition, similar to fish AFP (DeVries, *Annu. Rev. Physiol.* 45:245 (1983), the relationship between TH activity and THP concentration is hyperbolic. However, the ice crystals formed in the presence of THP are unusual in that they have a pronounced curvature of their surfaces. In contrast, ice crystals generated by fish AFP Types I and III are hexagonal bipyramids with flat, well-defined facets.

The purified, expressed THP protein can be directly added to an aqueous solution to depress the freezing point or in another embodiment, transformed organisms that express the antifreeze proteins can be added to items which will be stored frozen, such as frozen desserts. In yet another embodiment, the transformed organisms, e.g., fish, plants and yeast, need not express the THP proteins extracellularly but the presence of a THP gene and intracellular protein confers to them the increased ability to survive freezing temperatures. For example, a transformed organism can be a saltwater fish. Transformed salt-water fish can include members of the family Salmonidae, halibut, sablefish or any edible saltwater species not having any or sufficient levels of antifreeze proteins. Plants transformed with THP sequences can include grapes, oilseed plants such as canola, grains, citrus and sugar cane.

All publications, patents and patent applications cited herein are hereby expressly incorporated by reference for all purposes.

I. Definitions

The term "antibody" refers to a polypeptide substantially encoded by an immunoglobulin gene or immunoglobulin genes, or fragments thereof, which specifically binds to and recognizes an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$ a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into a Fab' monomer. The Fab' monomer is essentially a Fab with part of the hinge region (see, FUNDAMENTAL IMMUNOLOGY, 3RD ED., W. E. Paul, ed., Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

An "antifreeze protein antibody" is an antibody or antibody fragment that specifically binds an antifreeze protein of this invention or a subsequence thereof.

The term "antifreeze protein" refers to a protein found in the body fluids of some poikilothermic organisms, such as the *Tenebrio molitor* mealworm and plants, which have the commonly known property that they reduced non-colligatively the freezing point of water. Antifreeze proteins are also known as "thermal hysteresis proteins" (THPs). As used herein, "antifreeze proteins" or "THPs" includes chemically synthesized and recombinantly produced polypeptides having a protein sequence with substantial similarity to a naturally occurring antifreeze protein and retaining the properties of a natural antifreeze protein.

The phrase "consensus sequence" refers to a nucleic acid or amino acid sequence in which each position represents the residue or base most often found when many actual sequences are compared. SEQ ID NO:1 is a consensus sequence of a repeating motif found in the proteins of the instant invention The phrase "conserved amino acids" refers to common amino acid residues in two or more appropriately aligned THP-motif sequences. The conserved amino acid sequences can be intrapeptide or interpeptide. For example, in the THPs of the present invention, the amino acid motifs may consist of 5 out of 6 conserved amino acids, or in other words, 5 out of 6 amino acid residues of any particular motif will be common with 5 out of 6 amino acids of the motif either within a THP amino acid sequence or within two or more THP amino acid sequences.

The term "contiguous amino acid motif" refers to a repeating pattern of amino acids present in a polypeptide or protein. The amino acids in each repeat do not have to be the same but there should be a pattern common to all. For example, in the class of proteins of the present invention, the repeating amino acid motif; cys-thr-xaa-ser-xaa-xaa cys-xaa-xaa-ala-xaa-thr, where xaa is any amino acid, is present.

The term "crustacean" refers to the common definition of the word, i.e., a chiefly aquatic arthropod of the class Crustacea, including lobsters, shrimps, crabs and barnacles.

The term "decreasing the freezing point of an aqueous solution" refers to lowering the temperature of an aqueous solution at which ice crystals form and grow. The decrease in freezing point depends both on the agent used to decrease tile freezing point and its concentration in the aqueous solution. The freezing point depression increases as the antifreeze component is added to the aqueous solution, until a maximum depression is observed at a characteristic concentration. Further addition of antifreeze chemicals, such as ethylene glycol, to aqueous solutions will either result in insolubility of the antifreeze composition or serve to increase the freezing point of the mixture. On the other hand, the increase in thermal hysteresis with increased THP concentration is not linear but hyperbolic. The incremental increases in TH that result from unit increases in THP concentration become smaller and smaller as the saturation point of the THP solubility is approached.

The freezing point of a solution with a THP protein is defined as the temperature at which the sample being measured, which contains an ice crystal nucleator, becomes a solid mass of ice. The ice crystals can form spontaneously or expand from an ice nucleator. Spontaneous formation of a solid mass of ice without a nucleator is typically termed the "supercooling ability" of the THP. Because of the absence of an ice nucleator to initiate the ice formation process, supercooling can occur at much lower temperatures.

In addition to inspecting visually ice crystal formation, a thermal hysteresis assay can measure the difference between the freezing and melting points of a solution. The melting point of a solution is the temperature at which there is only one ice crystal left in a solution (see, infra, for a more complete description of TH activity).

The phrase "expressed externally" in the context of a recombinant protein refers to the ability of the transformed cell to synthesize and direct the protein into the extracellular matrix. The extracellular matrix can be the interstitial space between cells in a multicellular organism, bacterial broth or tissue culture medium. With bacteria, external expression can also include expression of the recombinant protein into the periplasm of the bacteria. External expression can be by any means, e.g., secretory and transport vesicles, expression as a membrane protein, expression of a cleavable signal peptide, etc.

The terms "homology," "sequence identity" and "sequence similarity" in the context of this invention mean that two peptide sequences, when optimally aligned, such as by the programs GAP or BESTFIT using default gap weights, share at least 40 percent sequence identity, preferably at least 50 percent sequence identity, and most preferably at least 60 percent sequence identity. "Percentage amino acid sequence identity" refers to a comparison of the amino acid sequences of two polypeptides which, when optimally aligned, have approximately the designated percentage of the same amino acids. For example, "60% sequence identity" and "60% homology" refer to a comparison of the amino acid sequences of two polypeptides which, when optimally aligned, have 60% amino acid identity. Preferably, residue positions which are not identical differ by conservative amino acid substitutions. For example, the substitution of amino acids having similar chemical properties such as charge or polarity is not likely to affect the properties of a protein. Examples include glutamine for asparagine or glutamic acid for aspartic acid.

The term "immunologically reactive conditions" refers to an environment in which antibodies can bind to antigens. Typically, this is an immunological binding assay.

The term "isolated," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis (PAGE) or high performance liquid chromatography (HPLC). A protein which is the predominant species present in a preparation is substantially purified.

In particular, an isolated THP gene is separated from open reading frames which naturally flank the gene and encode proteins other than the THP. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid molecule" or "nucleic acid sequence" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, and mRNA encoded by a gene.

The phrase "exogenous nucleic acid" generally denotes a nucleic acid that has been isolated, cloned and ligated or chemically synthesized and ligated to a nucleic acid with which it is not combined in nature, and/or introduced into and/or expressed in a cell or cellular environment other than the cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed.

The phrase "a nucleic acid sequence encoding" refers to a nucleic acid which contains sequence information for a structural RNA such as rRNA, or tRNA, or for mRNA which encodes the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant means" refers to techniques where proteins are isolated, wherein the cDNA sequence coding the protein is identified and inserted into an expression vector. The vector is then introduced into a cell and the cell expresses the protein. Recombinant means also encompasses the ligation of coding or promoter DNA from different sources into one vector for expression of a fusion protein, constitutive expression of a protein, or inducible expression of a protein.

The phrase "specifically or selectively binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example. antibodies raised against the THP of this invention or to the partially encoded sequence depicted in SEQ ID NO: 4 can be selected to specifically immunoreact with full length protein and not with other proteins except perhaps to polymorphic variants. As described below, a variety of immunoassay formats may be used to select antibodies specifically immunoreactive with a particular protein. For example, solid-phase ELISA immunoassays are routinely used to select monoclonal antibodies specifically immunoreactive with a protein. See Harlow & Lane (1988) ANTIBODIES, A LABORATORY MANUAL, Cold Spring Harbor Publications, New York ("Harlow & Lane"), for a description of immunoassay formats and conditions that can be used to determine specific immunoreactivity. Typically a specific or selective reaction will be at least twice background signal or noise and more typically more than 10 to 100 times background.

The term "specifically hybridizing" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook or CURRENT PROTOCOLS IN MOLECULAR BIOLOGY, Ausubel et al., ed. Greene Publishing and Wiley-Interscience, New York (1987) ("Ausubel").

"Stringent hybridization" and "stringent hybridization wash conditions" in the context of nucleic acid hybridization experiments such as Southern and northern hybridizations are sequence dependent, and are different under different experimental parameters. An extensive guide to the hybridization of nucleic acids is found in Tijssen (1993) LABORATORY TECHNIQUES IN BIOCHEMISTRY AND MOLECULAR BIOLOGY—HYBRIDIZATION WITH NUCLEIC ACID PROBES part I chapter 2 "Overview Of Principles Of Hybridization And The Strategy Of Nucleic Acid Probe Assays", Elsevier, New York. Generally, highly stringent hybridization and wash conditions are selected to be about 5° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "thermal hysteresis activity" or "TH activity" refers to the ability to alter the temperature difference (° C.) between the freezing and melting points of a solution containing ice. Preferably, TH activity is be measured by observation of ice crystal formation in a nanoliter osmometer following the procedure set forth in Lawson & Semler, Proc. Nat'l Acad. Sci. USA 88:9919 (1991). Alternatively, TH activity can be determined according to the method described in deVries, METHODS IN ENZYMOLOGY, VOL. 127, Packer (ed.), Academic Press, New York (1986) or a variation thereof.

For example, in the present invention, the TH activity of the native Tenebrio molitor THP from hemolymph at approximately 1 mg/mL is greater than approximately 5° C. The TH activity of the recombinant THP of this invention at approximately 1 mg/mL is about 5° C. or less. More preferably, the TH activity is lower than about 3° C. Most preferably, the TH activity is between 1.5 and 3° C. It is hypothesized that the differences between the TH activity of the native THP and the recombinant THP is due to imperfect folding of at least a portion of the THP of the bacteria-derived recombinant proteins. When properly folded, it is expected that the TH activities of the recombinant THP will be similar to that of the native THP.

II. Nucleic Acids Encoding THP

A. General Techniques

The nucleic acid compositions of this invention, whether RNA, cDNA, genomic DNA, or a hybrid of genetic recombinations, may be isolated from natural sources or may be synthesized in vitro. The nucleic acids claimed may be present in transformed cells, in a transformed cell lysate, or in a partially purified or substantially pure form.

Techniques for nucleic acid manipulation of genes encoding the antifreeze protein such as generating libraries, subcloning into expression vectors, labeling probes, DNA hybridization, and the like are described generally in Sambrook et al., MOLECULAR CLONING: A LABORATORY MANUAL (2ND ED.), Vols. 1-3, Cold Spring, Harbor Laboratory, N.Y. (1989) ("Sambrook"), which is incorporated herein by reference.

Nucleic acids and proteins are detected and quantified herein by any of a number of means well known to those of skill in the art. These include analytical biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR®, radiolabeling, scintillation counting, and affinity chromatography.

B. Isolation of Nucleic Acids Encoding THP

Methods of isolating total DNA or mRNA are well known to those of skill in the art. For example, methods of isolation and purification of nucleic acids are described in detail in Chapter 3 of LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, P. Tijssen, ed. Elsevier, N.Y. (1993) ("Tijssen").

1. Preparation and Screening of DNA Libraries

There are numerous methods for isolating the DNA sequences encoding the antifreeze protein of this invention. For example, DNA may be isolated from a genomic or cDNA library using labeled oligonucleotide probes having sequences complementary to the sequences or subsequences disclosed herein (SEQ ID NOs:2 or 5). Such probes can be used directly in hybridization assays to isolate DNA encoding THP isoforms. Alternatively probes can be designed for use in amplification techniques such as PCR, and DNA encoding THP may be isolated by using methods such as PCR (see infra).

To prepare a cDNA library, mRNA is isolated from *Tenebrio* larvae (Carolina Biological Supply, or a local pet or bait shop) or from embryonic, larval or possibly adult cells grown in tissue culture. cDNA is reverse transcribed from the mRNA according to procedures well known in the art and inserted into vectors. The vectors are transfected into a recombinant host for propagation, screening, and cloning. Methods for making and screening cDNA libraries are well known. See Gubler & Hoffman, *Gene* 25:263 (1983) and Sambrook, et al.

To make a genomic library, total DNA is extracted from the cells of the insect by well-known methods (see Sambrook, et al.) and then mechanically sheared or enzymatically digested to yield DNA fragments (e.g., of about 12-20 kb). The fragments are then separated by gradient centrifugation from undesired sizes and are inserted in bacteriophage-λ or other vectors. These vectors (e.g., phage) are packaged in vitro, as described in Sambrook, et al. Recombinant phage are analyzed by plaque hybridization as described in Benton & Davis, *Science*, 196: 180 (1977). Colony hybridization is carried out as generally described in Grunstein, et al., *Proc. Natl. Acad. Sci. USA.*, 72:3961 (1975).

DNA encoding THP is identified in either cDNA or genomic libraries by the ability to hybridize with nucleic acid probes, for example SEQ ID NO:2 or 5. Once identified, these DNA regions are isolated by standard methods familiar to those of skill in the art. Alternatively, RNA encoding antifreeze protein may be identified by its ability to hybridize to nucleic acid probes in northern blots. See, Sambrook, et al.

Oligonucleotides for use as probes are chemically synthesized according to the solid phase phosphoramidite triester method first described by Beaucage & Carruthers using an automated synthesizer, as described in Needham-VanDevanter, et al., *Nucleic Acids Res.* 12:6159 (1984). Purification of oligonucleotides is by either native acrylamide gel electrophoresis or by anion-exchange HPLC as described in Pearson & Regnier, *J. Chrom.* 255:137-149 (1983). The sequence of the synthetic oligonucleotide can be verified using the chemical degradation method of Maxam & Gilbert, *Methods in Enzymology*, 65:499 (1980).

Other methods known to those of skill in the art may also be used to isolate DNA encoding the antifreeze protein. See Sambrook and Ausubel for descriptions of other techniques that can be utilized for the isolation of DNA encoding specific protein molecules.

2. Amplification of Nucleic Acids Encoding THP

Frequently, it is desirable to amplify the nucleic acid sample prior to hybridization and subsequent subcloning. One of skill in the art will appreciate that whatever amplification method is used, if a quantitative result is desired, care must be taken to use a method that maintains or controls for the relative frequencies of the amplified nucleic acids. Suitable amplification methods include, but are not limited to: polymerase chain reaction, PCR (PCR PROTOCOLS, A GUIDE TO METHODS AND APPLICATIONS. Innis, et al., Academic Press, Inc. N.Y., (1990) ("Innis")), ligase chain reaction (LCR) (see Wu and Wallace, *Genomics*, 4:560 (1989) ("Wu"), Landegren et al., *Science*, 241:1077 (1988) ("Landegren") and Barringer et al., *Gene* 89:117 (1990) ("Barringer"); transcription amplification (Kwoh et al., *Proc. Natl. Acad. Sci. USA*, 86:1173 (1989) ("Kwoh")); and, self-sustained sequence replication (Guatelli. et al., *Proc. Nat. Acad. Sci. USA*, 87:1874 (1990) ("Guatelli")).

All of the above methods can be used to prepare DNA encoding antifreeze protein. In PCR techniques, oligonucleotide primers complementary to the two borders of the DNA region to be amplified are synthesized. The polymerase chain reaction is then carried out using the two primers (see, Innis). In the instant invention, because of the presence of repetitive motifs, the length of the THP subsequence encoded by the amplified product will depend on the template used. Because the N and C termini are unique (i.e., different nucleotide sequences from the repetitive motif), to amplify the full-length THP encoding sequence, the primers of SEQ ID NOs: 6 and 7 can be used.

PCR can be used in a variety of protocols to isolate nucleic acids encoding partial sequences of THP. In these protocols, appropriate primers and probes for amplifying DNA encoding partial sequences of THPs are generated from analysis of the DNA sequences listed herein. For example, the oligonucleotides of SEQ ID NOs:6, 7, 8 and 9 can be used in a PCR protocol to amplify regions of DNA which encodes THPs. Once such regions are PCR-amplified, they can be sequenced and labeled oligonucleotide probes can be prepared from the sequence obtained. These probes can then be used to isolate DNA encoding the complete THP from DNA libraries.

SEQ ID NO:2 and 5 represent isoforms of naturally occurring *Tenebrio molitor* THP cDNA. They are not complete DNA gene sequences. However, the partial antifreeze nucleic acid sequence of SEQ ID NO:2 or 5 can be completed according to standard methods well known to those of skill in the art. A preferred approach for DNA isolation is RACE. Briefly, this technique involves using PCR to amplify a cDNA sequence using a random 5' primer and a defined 3' primer (5' RACE) or a random 3' primer and a defined 5' primer (3' RACE). The amplified sequence is then subcloned into a vector where it is then sequenced using standard techniques. The RACE method is well known to those of skill in the art and kits to perform RACE are commercially available (e.g. 5' RACE System, GIBCO BRL, Grand Island, N.Y., USA).

3. Cloning of THP-Encoding Inserts into Bacteria

As described above, to prepare and screen genomic DNA total DNA is fragmented and inserted into bacteriophage. Once inserts containing antifreeze nucleic acid sequence of interest have been identified (by PCR, hybridization or the like), they are excised out of λ phage vectors and inserted into bacterial vectors for expansion. Typically, suitable bacterial vectors are known to practitioners in the art and are commercially available. The most suitable vector may depend on the bacteria to be used, the size of the insert, the method of detection of bacteria which contain the insert of interest and the preference of the practitioner.

To simplify identification of colonies of bacteria transformed with vectors containing the inserts, many vectors have restriction enzyme sites or other splicing sites located within a coding sequence for an enzyme, in particular, β-galactosidase. If an insert has successfully been inserted into the vector at the restriction or splicing sites, the encoded enzyme is inactivated. After transformation of the bacteria with the vector (see, infra), colonies grown in the presence of isopropyl β-D-thiogalactoside (IPTG) (a substrate for β-galactosidase) appear white, while the colonies derived from a bacteria which did not incorporate the insert appear blue. Thus, if the frequency of ligation of the insert into the vector was low, one can pick the few colonies that contain inserts over the many that will not.

The vectors are then introduced into variants of *Escherichia coli*. Methods used to introduce foreign DNA into bacterial cells are known to those of skill in the art, but the most frequently used are electroporation and heat shock of competent cells. Most typically, competent *E. coli* are provided commercially (for example from Invitrogen, San Diego, Calif.). Alternatively, the bacteria can be made competent to take up foreign DNA by techniques well known in the art (see, Sambrook, et al.). To introduce the vectors containing the insert of interest into bacteria, the competent bacteria undergo a heat shock process. Briefly, the bacteria are held in an ice water bath and after the DNA has been added, the temperature of the bacteria is raised to 40-50° C., preferably 42° C. The bacteria are returned to the ice bath and then cultured. For a more detailed description of introducing DNA into bacteria see Sambrook, et al., which is incorporated by reference herein.

The bacterial cultures are grown and then plated out on agar. Typically, the vector encodes a gene which confers resistance to an antibiotic to the transformed bacteria. Therefore, bacteria which have taken up the vector survive and form colonies on agar plates permeated with the antibiotic. The surviving colonies can be used to incubate broth and expanded into large cultures of transformed bacteria.

Plasmids and other vectors can be purified from bacterial lysates by methods well known in the art. Many commercial suppliers sell kits for purifying small circularized DNA (plasmids) from total bacterial DNA. These kits are easy to use and, by following the manufacturer's instructions, the yield is usually quite high.

4. Sequencing of THP DNA

Sequencing of newly isolated DNA will identify and characterize THP nucleic acid of the invention, this nucleic acid encoding THP species or allelic variations, the antifreeze proteins of the invention. A protein can be considered a THP protein isoform if it has at least 60% amino acid sequence identity to the *Tenebrio molitor* THP identified by SEQ ID NO:6 and SEQ ID NO:7.

THP coding sequences can be sequenced while they are still present as inserts in vectors or as inserts released and isolated from the vectors. THP-encoding inserts can be released from the vectors by restriction enzymes or amplified by PCR. For sequencing of the inserts to discover which inserts contain full length antifreeze coding sequences, primers based on the N- or C-terminus, such as those of SEQ ID NO:8 and SEQ ID NO:9, or insertion points in the original λ-phage, can be used as primers. Most preferably, additional primers are synthesized to provide for overlapping sequences. Typically, dideoxy sequencing is done (Sequenase®, U.S. Biochemical). However, other kits and methods are available and known to those of skill in the art.

As an alternative to the bacterial cloning described above, the positive λ-phage plaques from the cDNA library can be subjected to in vivo excision with helper phage, for example R408 (Stratagene). The double stranded DNA can then be purified and sequenced or amplified by PCR using primers derived from the λ-phage.

C. Nucleic Acid Hybridization Techniques

The hybridization techniques disclosed herein can be utilized to identify, isolate and characterize genes and gene products (i.e., mRNA) encoding for the antifreeze proteins of the invention, including different THP species and allelic variations.

A variety of methods for specific DNA and RNA measurement using nucleic acid hybridization techniques are known to those of skill in the art. See NUCLEIC ACID HYBRIDIZATION, A PRACTICAL APPROACH, Ed. Hames, B. D. and Higgins, S. J., IRL Press, 1985; Gall & Pardue, *Proc. Natl. Acad. Sci.*, U.S.A. 63:378 (1969); John, et al., Nature 223:582 (1969); and Sambrook, et al. The selection of a hybridization format is not critical.

For example, one method for evaluating the presence or absence of DNA encoding antifreeze protein in a sample involves a Southern transfer. Briefly, digested genomic DNA is run on agarose slab gels in buffer and transferred to membranes. Hybridization is carried out using nucleic acid probes. For the THP of this invention, the nucleic acid probes can be designed based on conserved nucleic acid sequences amongst the class of proteins. Preferably nucleic acid probes are 20 bases or longer in length. (See Sambrook, et al. for methods of selecting nucleic acid probe sequences for use in nucleic acid hybridization.) In the instant invention, preferable probes would be the sequences identified as SEQ ID NO:2 or 5 or the entire coding region of any of the isoforms. Visualization of the hybridized portions allows the qualitative determination of the presence or absence of DNA encoding antifreeze protein.

Similarly, a northern transfer may be used for the detection of mRNA encoding antifreeze protein. In brief, mRNA is isolated from a given cell sample using one of a variety of extraction methods such as an acid guanidinium-phenol-chloroform. The mRNA is then electrophoresed to separate the mRNA species and the mRNA is transferred from the gel to a membrane. As with the Southern transfers, labeled probes are used to identify the presence or absence of THP mRNAs.

Sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography or autofluorography with $^3$H, $^{125}$I, $^{35}$S, $^{14}$C, or $^{32}$P-labeled probes or the like. Other labels include ligands which bind to labeled antibodies, fluorophores, chemiluminescent agents, enzymes, and antibodies which can serve as specific binding pair members for a labeled ligand. Detection would then depend on the label used.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to tile antibodies or, in some cases, by attachment to a radioactive label (see, Tijssen).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including PCR, LCR, Qβ-replicase amplification and other RNA polymerase mediated techniques (e.g., NASBA™) are found in Berger, Sambrook, and Ausubel, as well as Mullis et al., U.S. Pat. No. 4,683,202; Arnheim & Levinson, C&EN 36 (1990); Lomell et al., J. Clin. Chem., 35:1826 (1989); Van Brunt, Biotechnology 8:291-294 (1990); Wu & Wallace, Gene 4:560 (1989); Sooknanan & Malek, Biotechnology 13:563 (1995); Innis; Kwoh; Guatelli; Landegren; and Barringer. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, as gene probes in diagnostic methods, or as inhibitor components (see below) are typically synthesized chemically according to the solid phase phosphoramidite triester method described by Beaucage and Caruthers, e.g., using an automated synthesizer, as described in Needham-VanDevanter. Purification of oligonucleotides, where necessary, is typically performed by native acrylamide gel electrophoresis or by anion-exchange HPLC as described in Pearson & Regnier. The sequence of the synthetic oligonucleotides can be verified using the chemical degradation method of Maxam & Gilbert.

It will be appreciated that nucleic acid hybridization assays can also be performed in an array-based format. In this approach, arrays bearing, a multiplicity of different "probe" nucleic acids are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see, e.g., Jackson, et al., Nature Biotechnology 14:1685 (1996), and Chee, et al., Science 274:610 (1995)).

An alternative means for determining the level of expression of a gene encoding a protein in situ hybridization. In situ hybridization assays are well known and are generally described in Angerer, et al., Methods Enzymol., 152:649 (1987). In an in situ hybridization assay, cells or tissues are fixed to a solid support, typically a glass slide. If DNA is to be probed, the cells are denatured with heat or alkali. The cells are then contacted with a hybridization solution at a moderate temperature to permit annealing of labeled probes specific to the nucleic acid sequence encoding the protein. The probes are preferably labeled with radioisotopes or fluorescent reporters.

D. Expression of THP

After the coding region of an antifreeze protein gene has been identified, the expression of natural or synthetic antifreeze-encoding nucleic acids can be achieved by operably linking the coding region of an antifreeze protein gene to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, Gene 8:81 (1979); Roberts, et al., Nature 328:731 (1987); Berger & Kimmel, GUIDE TO MOLECULAR CLONING TECHNIQUES, METHODS IN ENZYMOLOGY, Vol 152, Academic Press, Inc., San Diego, Calif. ("Berger"); Schneider, et al., Protein Expr. Purif. 6435:10 (1995); Sambrook and Ausubel. Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia Biotech (Piscataway, N.J.), CLONTECH Laboratories, Inc. (Palo Alto, Calif.), Aldrich Chemical Company (Milwaukee, Wis.), GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acids (e.g., promoters and vectors) used in the present method can be isolated from natural sources, obtained from such sources as ATCC or GenBank libraries, or prepared by synthetic methods. Synthetic nucleic acids can be prepared by a variety of solution or solid phase methods. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Carruthers, et al., U.S. Pat. Nos. 4,458,066 and 4,500,707; Beaucage & Caruthers; Matteucci; Carruthers, et al., Genetic Engineering 4:1 (1982); Jones, chapter 2, Atkinson, et al., chapter 3, and Sproat, et al., chapter 4, in OLIGONUCLEOTIDE SYNTHESIS: A PRACTICAL APPROACH, Gait (ed.), IRL Press, Washington D.C. (1984); Froehler, et al., Tetrahedron Lett. 27:469 (1986); Froehler, et al., Nucleic Acids Res. 14:5399 (1986); Sinha, et al., Tetrahedron Lett. 24:5843 (1983); and Sinha, et al., Nucl. Acids Res. 12:4539-4557 (1984), which are incorporated herein by reference.

There are several well-known methods of introducing nucleic acids into bacterial cells, any of which may be used in the present invention (see Sambrook, et al.). These can include fusion of the recipient cells with bacterial protoplasts containing the DNA, DEAE dextran, infection with viral vectors, and the like.

The in vitro delivery of nucleic acids into bacterial hosts can be to any cell grown in culture. Contact between the cells and the genetically engineered nucleic acid constructs, when carried out in vitro, takes place in a biologically compatible medium. The concentration of nucleic acid varies widely depending on the particular application, but is generally between about 1 µM and about 10 mM. Treatment of the cells with the nucleic acid is generally carried out at physiological temperatures (about 37° C.) for periods of time of from about 1 to 48 hours, preferably of from about 2 to 4 hours.

Bacterial strains which can be used to express exogenous nucleic acid include Escherichia coli, Streptococcus cremoris, Streptococcus lactis, Streptococcus thermophilus, Leuconostc citrovorum, Leuconostoc mesenteroides, Lactobacillus acidophilus, Lactobacillus lactis, Bifidobacterium bifidum, Bifidobacterium breve, and Bifidobacterium longum.

In addition to bacterial expression systems, the THP of this invention can be expressed in other systems, in particular yeast and baculovirus, but also in mammalian and plant cells. The system used will depend on the lack of success in other systems, the ability to fold the THP properly, and the eventual use of the THP. For example, if the THP are to be used to protect bread dough yeast from freezing (see, U.S. Patent No. 5,118,792), a yeast system will be used. Yeast strains which can be used to express exogenous nucleic acid include *Torulopsis holmil, Saccharomyces fragilis, Saccharomyces cerevisiae, Saccharomyces lactis*, and *Candida pseudotropicalis*. If plants which can live through freezing temperatures are desired, transgenic techniques can be used to make transgenic plants. In addition, as will be described below, there may be uses for THP in animals, including insects, fish and crustaceans. However, of course, the system used should give THP with comparable thermal hysteresis activity to that found in the *Tenebrio* larvae.

As an example of alternative expression systems, International Publication WO 96/11586 (U.S. patent application Ser. No. 08/321,991, filed Oct. 12, 1994), which is incorporated by reference herein, describes the use of fish AFP-transformed *Lactobacillus bulgaricus* and *Streptococcus thermophilus* to secrete AFP in order to prevent ice recrystallization in fermented frozen foods, in particular frozen yogurt.

1. Preparation of Recombinant Vectors

To use isolated sequences in the above techniques, recombinant DNA vectors suitable for transformation of cells are prepared. Techniques for transforming a wide variety of animal and plant cells are well known and described in the technical and scientific literature. See, for example, Weising, et al., *Ann. Rev. Genet.* 22:421 (1988) for plant cells and Sambrook for animal and bacterial cells.

A DNA sequence coding for the desired antifreeze protein, for example a cDNA sequence encoding the full length THP, will preferably be combined with transcriptional and translational initiation regulatory sequences which will direct the transcription of the sequence from the gene in the cells or the intended tissues of the transgenic higher organism. A wide variety of well known transcriptional regulatory elements such as promoters and enhancers can also be included in the vectors selected to express a THP of the invention. Promoters which direct the THP of this invention in their native state can be identified by analyzing the 5' sequences of a genomic clone corresponding to the antifreeze protein genes described herein. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation.

In construction of recombinant expression cassettes of the invention, a promoter fragment, either related to the THP of this invention or heterologous to the THP, may be employed which will direct expression of the gene in all tissues of a transgenic organism. Such promoters are referred to herein as "constitutive" promoters and are active under most environmental conditions and states of development or cell differentiation. Examples of constitutive promoters of plants include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the promoter may direct expression of the polynucleotide of the invention in a specific tissue (tissue-specific promoters) or may be otherwise under more precise environmental control (inducible promoters). Examples of tissue-specific plant promoters under developmental control include promoters that initiate transcription only in certain tissues, such as fruit, seeds, or flowers. The tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on transformed cells. For example, the marker may encode antibiotic resistance, particularly resistance to kanamycin. G418, bleomycin or hygromycin.

Plants can be transformed using viral vectors, such as, for example, the tobacco mosaic virus, to express THP proteins of the invention. Selection and construction of vectors and techniques for transforming a wide variety of plant cells are well known, for example, see Hamamoto, et al., U.S. Pat. No. 5,618,699.

2. Production of Transgenic Organisms

DNA constructs of the invention may be introduced into the genome of a host by a variety of conventional techniques. For example, in plants, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. As discussed above, plant virus vectors such as tobacco mosaic virus containing the THP sequences of the invention can be used to innoculate a plant. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

*Agrobacterium tumefaciens*-mediated transformation techniques, including disarming and use of binary vectors, are well described in the scientific literature. See, for example Horsch, et al., *Science* 233:496 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype, such as increased tolerance to freezing. The transformed plants of the invention can also be employed as "living factories" to express an antifreeze protein in substantial quantities. Such plant regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124-176, Macmillian Publishing Company, New York, 1983; and Binding, REGENERATION OF PLANTS, PLANT PROTOPLASTS, pp.21-73. CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467 (1987).

To produce a transgenic plant or animal, for example a salt-water fish, microinjection techniques are known in the art and well described in the scientific and patent literature. The introduction of DNA constructs into cells using polyethylene glycol precipitation is described in Paszkowski, et al., *EMBO J.* 3:2717 (1984). Electroporation techniques are described in Fromm, et al., *Proc. Natl. Acad. Sci. USA* 82:5824 (1985). Ballistic transformation techniques are described in Klein, et al., *Nature* 327:70 (1987).

III. Detection and Characterization of the Class of THP of this Invention

By the assays described below, the THP of this invention share characteristics with a thermal hysteresis protein isolated from final larval instar *Tenebrio molitor* hemolymph. These assays are used to define whether other novel THP are sufficiently related to the prototype proteins YL-1 through YL-4 so as to fall within the scope of this invention. The assays can also be used to detect and quantify THPs present in bacteria broth, tissue culture fluid and plant and animal tissues.

A. Detection of THP

Expressed THP may be detected or quantified by a variety of methods. Preferred methods involve the use of functional activity assays and immunological assays utilizing specific antibodies.

1. Antibodies

Methods of producing polyclonal and monoclonal antibodies are known to those of skill in the art. See, e.g., Coligan, CURRENT PROTOCOLS IN IMMUNOLOGY, Wiley/Greene, NY (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler & Milstein, *Nature* 256:495 (1975); and Harlow and Lane. Such techniques include antibody preparation by selection of antibodies from libraries of recombinant antibodies in phage or similar vectors. See, Huse et al., *Science* 246:1275 (1989) ("Huse"); and Ward et al., *Nature* 341:544 (1989).

To produce large amounts of antibodies for use in, for example, immunoaffinity purification, a number of immunogens may be used. THP from *Tenebrio molitor* or from the transformed cells as described in this invention are the preferred immunogens for the production of monoclonal or polyclonal antibodies. Naturally occurring antifreeze protein from other organisms may also be used either in pure or impure form. Synthetic peptides made using a fragment of antifreeze protein sequence described herein may also used as an immunogen for the production of antibodies to the protein. The peptides can be used alone or conjugated to another composition.

Methods of production of polyclonal antibodies are known to those of skill in the art. In brief, an immunogen is mixed with an adjuvant, as described above, and animals are immunized. The animal's immune response to the immunogen preparation is monitored by taking test bleeds and determining the titer of reactivity to the immunogen. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Large amounts of monoclonal antibodies for use in immunoaffinity purification or immunoassays may be obtained by various techniques familiar to those skilled in the art. Briefly, spleen cells from an animal immunized with a desired antifreeze protein are immortalized, commonly by fusion with a myeloma cell (See, Kohler & Milstein, *Eur. J. Immunol.* 6:511 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for THP. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined in Huse.

The concentration of THP can be measured by a variety of immunoassay methods. For a review of immunological and immunoassay procedures in general, see Stites. Moreover, the immunoassays of the present invention can be performed in any of several configurations, which are reviewed extensively in ENZYME IMMUNOASSAY, E. T. Maggio, ed., CRC Press, Boca Raton, Fla. (1 980); Tijssen; and Harlow and Lane, each of which is incorporated herein by reference.

For example, in order to produce antisera for use in an immunoassay for antifreeze protein, YL-1, YL-2, YL-3, YL-4 or fragments thereof, are isolated as described herein. An inbred strain of mice or rabbits is immunized with the above antifreeze isoforms or polypeptide of SEQ ID NO:4 using a standard adjuvant, such as Freund's adjuvant, and a standard immunization protocol. Alternatively, a synthetic peptide derived from the sequences disclosed herein and conjugated to a carrier protein can be used an immunogen. Polyclonal sera are collected and titered against the THP in an immunoassay, for example, a solid phase immunoassay with the THP immobilized on a solid support. Polyclonal antisera with a $K_a$ of $10^{-1}$ $M^{-1}$ or greater are selected and tested for their cross reactivity against homologous proteins from other organisms and/or non-antifreeze protein, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

2. Immunological Binding Assays

In a preferred embodiment, THP are detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY Vol. 37: *Antibodies in Cell Biology*, Asai, ed. Academic Press, Inc. New York (1993); and Stites. Immunological binding assays (or immunoassays) typically utilize a "capture agent" to specifically bind to and often immobilize the analyte (in this case THP or a fragment thereof). The capture agent is a moiety that specifically binds to the analyte. In a preferred embodiment, the capture agent is an antibody that specifically binds to THP. The antibody (anti-THP) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled THP polypeptide or a labeled anti-THP antibody. Alternatively, the labeling agent may be a third moiety, such as another antibody, that specifically binds to the antibody/THP complex.

In a preferred embodiment, the labeling agent is a second THP antibody bearing a label. Alternatively, the second THP antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401-1406 (1973), and Akerstrom, et al., *J. Immunol.* 135:2589-2542 (1985)).

Throughout the assays, incubation and/or washing, steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 4° C. to 40° C.

a. Non-Competitive Assay Formats.

Immunoassays for detecting THP may be either competitive or noncompetitive. Noncompetitive immunoassays are assays in which the amount of captured analyte (in this case THP) is directly measured. In one preferred "sandwich" assay, for example, the capture agent (anti-THP antibodies) can be bound directly to a solid substrate where they are immobilized. These immobilized antibodies then capture protein present in the test sample. The THP thus immobilized is then bound by a labeling agent, such as a second THP antibody bearing a label. Alternatively, the second THP antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

b. Competitive Assay Formats.

In competitive assays, the amount of analyte (THP) present in the sample is measured indirectly by measuring the amount of an added (exogenous) analyte (THP) displaced (or competed away) from a capture agent (anti THP antibody) by the analyte present in the sample. In one competitive assay, a known amount of, in this case THP, is added to the sample and the sample is then contacted with a capture agent, in this case an antibody that specifically binds THP. The amount of THP bound to the antibody is inversely proportional to the concentration of THP present in the sample.

In a particularly preferred embodiment, the antibody is immobilized on a solid substrate. The amount of THP bound to the antibody may be determined either by measuring the amount of THP present in an THP/antibody complex, or alternatively by measuring the amount of remaining uncomplexed THP. The amount of THP may be detected by providing a labeled THP molecule.

A hapten inhibition assay is another preferred competitive assay. In this assay a known analyte, in this case THP, is immobilized on a solid substrate. A known amount of anti-THP antibody is added to the sample, and the sample is then contacted with the immobilized THP. In this case, the amount of anti-THP antibody bound to the immobilized THP is inversely proportional to the amount of THP present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding formant can be used for crossreactivity determinations to permit one of skill to determine if a novel THP is sufficiently related to the claimed THP so as to fall under the claims of this invention. For example, a THP fragment of SEQ ID NO:4 can be immobilized to a solid support. Proteins are added to the assay which compete with the binding of the antisera to the immobilized antigen. The ability of the proteins to compete with the binding of the antisera to the immobilized THP is compared to the binding by the same THP as was used to coat the solid support. The percent crossreactivity for the above proteins is calculated, using standard calculations. Those antisera with less than 10% crossreactivity with the THP of SEQ ID NO:4 are selected and pooled. The cross-reacting antibodies are optionally removed from the pooled antisera by immunoabsorption with the above proteins.

The immunoabsorbed and pooled antisera can be used in a competitive binding immunoassay, as described above, to analyze whether a second protein is an antifreeze protein of this invention. In the competitive binding immunoassay the protein, or immunogen, used to develop the antiserum competes with a second, uncharacterized protein or peptide in an antibody binding reaction. The two proteins are each assayed at a wide range of concentrations and the amount of each protein required to inhibit 50% of the binding of the antisera to the immobilized protein is determined. If the amount of the second protein required is less than 10 times the amount of the characterized immunogen (for example, SEQ ID NO:2, SEQ ID NO:4 or an immunogenic fragment thereof) that is required, then the second protein is said to specifically bind to an antibody generated to that characterized (antifreeze protein) immunogen.

c. Other Assay Formats.

Western blot (immunoblot) analysis can be used to detect and quantify the presence of antifreeze protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind THP. The anti-THP antibodies specifically bind to THP on the solid support. These antibodies may be directly labeled or alternatively may be subsequently detected using labeled antibodies (e.g., labeled sheep anti-mouse antibodies) that specifically bind to tile anti-antifreeze protein.

In addition to using nucleic acid probes for identifying novel forms of the class of proteins claimed herein, it is possible to use antibodies to probe expression libraries. This is a well known technology (See Young & Davis, *Proc. Nat'l Acad. Sci. USA* 80:1194 (1982)). In general, a cDNA expression library may be prepared from commercially available kits or using readily available components. Phage vectors are preferred, but a variety of other vectors are available for the expression of protein. Such vectors include but are not limited to yeast, animal cells and *Xenopus* oocytes. One selects mRNA from a source that is enriched with the target protein and creates cDNA which is then ligated into a vector and transformed into the library host cells for immunoscreening.

Screening involves binding and visualization of antibodies bound to specific proteins on cells or immobilized on a solid support such as nitrocellulose or nylon membranes. Positive clones are selected for purification to homogeneity and the isolated cDNA then prepared for expression in the desired host cells. A good general review of this technology can be found in METHODS OF CELL BIOLOGY, VOL. 37 entitled *Antibodies in Cell Biology*, Assai (ed.) 1993.

Where the antibodies are generated to protein like the THPs of this invention, which are rich in cysteine and hypothetically contain many disulfide bridges, the test proteins are optionally denatured to fully test for selective binding and it may be best to measure the test proteins against proteins of similar size, e.g., one would test a full length THP against a prototype full length THP even though the antisera was generated against a fragment of the prototype THP. This simplifies the test and avoids having to take into account conformational problems and molecular weight/molar concentrations in the determination of the results from the competitive immunoassays.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34 (1986)).

B. Purification of THP

The polypeptides of this invention may be purified to substantial purity by standard techniques, from a variety of sources such as larval hemolymph, tissue culture media, transgenic plants and animals, yeasts and bacteria. For standard purification procedures, including selective precipitation with such substances as ammonium sulfate; column chromatography, immunopurification methods, and others see, for instance, Scopes, PROTEIN PURIFICATION: PRINCIPLES AND PRACTICE, Springer-Verlag: New York (1982), U.S. Pat. No. 4,673,641, Ausubel, and Sambrook, all incorporated herein by reference. 1. Purification of THP from Bacterial Cultures In the case of secreted proteins, the protein of interest can be isolated and purified from the broth in which bacteria have been grown without having to resort to the cell lysis methods detailed below.

2. Purification of THP from Bacterial Cytoplasm and Periplasm

After expression of THP in *E. coli*, the protein may be found in the periplasm, cytoplasm or inclusion bodies of the bacteria. The periplasmic fraction of the bacteria can be isolated by cold osmotic shock in addition to other methods known to those of skill in the art (see Ausubel, and Trayer, & Buckley, *J. Biol. Chem.* 245(18):4842 (1970)).

To isolate proteins from the periplasm and cytoplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. Alternatively, the bacteria can be lysed by sonication. The proteins present in the supernatant can be separated from the host proteins by standard separation techniques well known to those of skill in the art.

3. Purification of Inclusion Bodies

When recombinant proteins are expressed by the transformed bacteria in large amounts, typically after promoter induction; but expression can be constitutive, the proteins may form insoluble aggregates.

Purification of aggregate proteins (hereinafter referred to as inclusion bodies) involves the extraction, separation and/or purification of inclusion bodies by disruption of bacterial cells, typically but not limited by, incubation in a buffer of about 100-150 µg/mL lysozyme and 0.1% NONIDET P40®, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel and Sambrook and will be apparent to those of skill in the art.

The cell suspension is centrifuged and the pellet containing the inclusion bodies resuspended in buffer, e.g., 20 mM Tris-HCl (pH 7.2), 1 mM EDTA, 150 mM NaCl and 2% TRITON-X 100®, a non-ionic detergent. It may be necessary to repeat the wash step to remove as much cellular debris as possible. The remaining pellet of inclusion bodies may be resuspended in an appropriate buffer (e.g. 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties) together with a reducing agent such as DTT. The proteins that formed the inclusion bodies can then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein.

After solubilization, the protein can be separated from other bacterial proteins by standard separation techniques.

4. Standard Protein Separation Techniques a. Solubility Fractionation

Often as an initial step and if the protein mixture is complex, an initial salt or organic solvent fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

b. Size Differential Filtration

If the size of the protein of interest is known or can be estimated from the cDNA sequence, proteins of greater and lesser size can be removed by ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

c. Column Chromatography

Proteins can be separated on the basis of their size, net surface charge, hydrophobicity and affinity for ligands. In addition, antibodies raised against proteins can be conjugated to column matrices and the proteins immunopurified. All of these methods are well known in the art. See Scopes, R. K., Protein Purification: Principles and Practice, 2nd ed., Springer Verlag, (1987).

It will be apparent to one of skill that chromatographic techniques can be performed at any scale and using equipment from many different manufacturers (e.g., Pharmacia Biotech).

In a preferred embodiment, the purification of THP from *E. coli* supernatant is accomplished in part by gel filtration, and protein concentrations are determined according to a number of techniques. e.g., Bradford, *Anal. Biochem.* 72:248-257 (1976).

d. Amino Acid Sequence

The amino acid sequences of the THP of this invention can be determined by, for example, Edman degradation, a technique which is well known in the art. By Edman degradation, an internal section of THP was sequenced spanning a repeating motif of 12 contiguous amino acids which was found to make up the bulk of the THP. This motif (SEQ ID NO:1) is repeated at least 5 times and more preferably 5 to 12 times in each isoform.

In addition to the internal sequencing, N-terminal sequencing can be performed by techniques known in the art. However, in the native THP26 and by analogy in 3 of the recombinant THP isoforms, the N terminus was blocked. By nucleic acid sequencing, the N termini were determined to be a glutamine which would be consistent with N-terminal sequencing being blocked by pyroglutamate (cyclized glutamine). The deduced N-termini of the class of THP of this invention is identified as SEQ ID NO:4.

e. Molecular Weight/Isoelectric Point

The molecular weight of a protein can be determined by many different methods, all known to one of skill in the art. Some methods of determination include: SDS gel electrophoresis, native gel electrophoresis, molecular exclusion chromatography, zonal centrifugation, mass spectroscopy, and calculation from sequencing. Disparity between results of different techniques could be due to factors inherent in the technique. For example, native gel electrophoresis, molecular exclusion chromatography, zonal centrifugation depend factors such as the size, shape and net charge of the protein. The proteins of this invention are rich in cysteine and might be expected to form many disulfide bonds, both intra- and intermolecular. SDS gel electrophoresis depends on the binding of SDS to amino acids present in the protein. Some amino acids bind SDS more tightly than others, therefore, proteins will migrate differently depending on their amino acid composition. In the instant invention, because the THP disclosed herein are repeating units of a motif, the relative number of different amino acids is quite small and could result in a large disparity in molecular weight by SDS gel electrophoresis. The calculated molecular weight from the sequence utilizes the frequency of amino acids present in the protein and multiplies that frequency by the molecular weight of the amino acid. If the protein is glycosylated, calculated molecular weight will not reflect this and mass spectroscopy may be a necessary alternative.

In the present invention, the apparent molecular weight of the class of THP by molecular exclusion chromatography was between 17 and 19 kD; by SDS gel electrophoresis, 22-30 kD. By mass spectroscopy, the molecular weight of the class of proteins was found to be between 7 to 12, preferably 8 to 11 and most preferably from about 8.4 to 11.7 kD. This agreed with the results obtained when the molecular weight was calculated from the amino acid sequencing. By comparing the amino acid sequences and the molecular weights by mass spectroscopy, it is likely that the differences in molecular weight are due largely to different number of motif repeats.

The isoelectric point of a protein can be determined by native gel (or disc) electrophoresis, isoelectric focussing or in a preferred method, by calculation given the amino acid content of the protein. The class of proteins of the instant invention have a calculated pI of about 8 to 10.

f. Functional Assays

The THP species and isoforms of the invention can be identified and characterized by at least two functional properties, for example, thermal hysteresis and unique formation of ice crystals:

(1) Thermal Hysteresis

The proteins of this invention are approximately 100 fold more active than known fish antifreeze proteins in a thermal hysteresis assay. Thermal hysteresis is defined as the difference between the solution freezing and melting temperatures. Freezing point is taken as the temperature at which uncontrollable ice growth occurs from a seed ice crystal. Melting point is taken as the warmest temperature at which an ice crystal can be stably held without melting. TH activity can be measured in a nanoliter osmometer (Clifton Technical Physics, Martford, N.Y.) by methods well known in the art (see, for example. Chakrabartty & Hew, *Eur. J. Biochem.* 202:1057 (1991)). The starting ice crystal is usually 20-50 µm in diameter. The buffer used is typically 100 mM $NH_4HCO_3$ (pH 7.9) but other buffers of similar osmolarity can be used. Alternatively, TH activity can be measured in bacterial broth, tissue culture fluid, or hemolymph.

The osmometer is a thermal electric cooling module with a separate but linked variable temperature control. This apparatus allow temperature regulation in the 0° C. to −9° C. range with a deep freeze mode to −40° C. The cooling module can be set up on a microscope stage where the growth and melt behavior of an ice crystal can be observed directly. The sample holder can be a small plate with dimensions of about 7 mm×7 mm×0.75 mm containing multiple small sample holes (about 0.35 mm in diameter). A drop of immersion oil, such as Cargille's B immersion oil, can be placed on the underside of the sample holder so that the sample holes are filled. 1 to 5 nL samples are then delivered into the center of the oil-filled hole by a capillary tube.

To measure TH activity, the samples are first frozen by cooling the samples rapidly to −40° C. and then allowing them to warm up to the melting point temperature. Once the melting point is reached, the samples are cooled by approximately 0.02° C. (10 milli-osmoles or mosmoles) per 10-15 seconds until the freezing temperature is reached. The conversion from the unit "osmos" to "° C." is 1.00 osmoles equals 1.86° C. In most instances, when the freezing point of a THP sample is reached, the ice crystal within the sample will grow spontaneously and rapidly. This leads to freezing of the entire sample.

Alternatively, a small ice crystal can be frozen onto the surface of a solution and the temperature of the solution immediately reduced to below freezing. The temperature below freezing when the nucleated ice crystal begins to grow is the freezing point depression or the thermal hysteresis measurement (see, Patterson & Duman, *J. Exp. Zool.* 210:361 (1979); and Wu, et al., *J. Comp. Physiol. B* 161:271 (1991). The thermal hysteresis activity of a solution is dependent on the concentration of the antifreeze protein, with the greater the concentration of the protein, the greater the activity shown by the solution. However, increased concentrations of THPs produce incrementally smaller increases in TH activity and a maximum is approached. In other words, the relationship between THP concentration and TH is hyperbolic, not linear.

The proteins of the present invention preferably have thermal hysteresis values greater than 1.0° C. at about 1 mg/mL, more preferably greater than 1.5° C. at about 1 mg/mL and most preferably between about 1.5-3.0° C. at about 1 mg/mL.

(2) Unique Formation of Ice Crystals

In addition to having approximately 100 fold more specific activity than previously known fish antifreeze proteins, the proteins of this invention produce different shaped ice crystals. Under microscopic analysis, fish antifreeze proteins produce ice crystals which are hexagonal bipyramids with flat, well-defined facets. The THP of this invention, on the other hand, form crystals with rounded edges, preferably oval-shaped and with non-flat surfaces, preferably convex.

IV. Use of Antifreeze Proteins and Related Genes

The proteins or genes encoding the THP may be used in ways to suppress ice crystal growth. For a comprehensive review of uses of antifreeze proteins, see U.S. Pat. No. 5,118,792. The THP of this invention may be introduced in the protein form, or they may be introduced as genes which are expressed endogenously at a level which should be attainable by expressing an antifreeze protein in a cell under the control of a suitable strong promoter to produce the proteins. Suitable concentrations of THP will vary depending on the use, but will typically be in the range of from about one part per billion to about one part per thousand (i.e. 1 μg/L to 1 g/L).

In one embodiment of the invention, the proteins will be introduced to foodstuffs. This has a number of different aspects. One is the introduction into plant foodstuffs, either into the entire plant and thus conferring some degree of general resistance to damage from subfreezing climatic conditions, or into a plant part such as the fruit or vegetable portion to minimize damage specifically to those particular plant organs upon freezing. Exemplary plant parts are stems, roots, leaves, flowers, petioles, pericarp, seeds, vegetative tissue, tubers and so forth.

The texture, taste, and useful storage life of frozen vegetables will be improved, for example, celery, potatoes, asparagus, peas, carrots, beans, broccoli, sweet corn and spinach. Similarly, the texture, taste and useful storage life of fruits will be enhanced, including strawberries, blueberries, raspberries, citrus fruits, bananas, grapes, kiwis, peaches, pineapples, plums, cherries, tomatoes and mangoes.

This introduction into plant and other products may be most easily accomplished by genetic introduction of appropriate nucleic acids into the target organism. Expression of the nucleic acid, either constitutively or inducibly, before food processing has begun, or after harvesting and processing has begun, may lead to sufficiently high levels of the polypeptide to effectively protect the foodstuff, such as up to 0.5%, but more preferably up to about 0.1% of total plant protein by mass. Expression can also be on a tissue specific basis. For example, linkage to ripening genes in fruits may result in expression even after harvesting from the producing plant.

The polypeptides may also be added into foods which are expected to be frozen. Many frozen foods are intended to be consumed in the cold state, for example, ice cream, frozen yogurt, ice milk, sherbet, popsicles, frozen whipped cream, frozen cream pies, frozen puddings and the like. In particular, texture and flavor are adversely affected by the formation of large ice crystals throughout a freeze-thaw cycle that occurs in most home frost-free freezers or upon sustained storage in the frozen state. This ice crystal growth process may be prevented entirely, or at least minimized by tile addition of antifreeze polypeptides. The purified antifreeze protein may be either incorporated throughout the foodstuff, or may, alternatively, be applied to the surface where condensation and crystal formation is expected to occur most readily.

In another embodiment, the genes that encode the THP of this invention are used to transform microorganisms which when added to foodstuffs, protect the foodstuffs or the microorganism from freezing. For example, bacteria such as *Streptococcus thermophilus* and *Lactobacillus bulgaricus* can be added to dairy products that is intended to be sold as frozen yogurt. In addition to fermenting the dairy products to produce yogurt, the THP expressed by the bacteria will protect the product from home freezer freeze-thaw cycles and produce a more palatable product.

Another use would be to transform dough yeast with nucleic acids encoding THP. Upon incorporation and expression of this gene into the yeast, and use of these yeast in frozen dough, the dough will naturally leaven upon thawing because the yeast viability will remain high upon thawing. Because less damage accumulates from storage in the presence of these antifreeze polypeptides and thawed samples preserve high viability, either longer storage times will be possible, or perhaps much smaller aliquots will need to be stored.

There are various embodiments not specific to the food freezer. One is the use of THP to protect plants from climatic freezing conditions. The THP may be either internally incorporated into the cytoplasm by expression of an introduced gene, or the proteins may be externally applied to the plants. External application may be achieved either by direct application of the proteins to the plant, or by the external deposit onto the plant of an organism which secretes the proteins. These same alternatives for introduction apply to other uses as well.

In addition to plants, it is envisioned that the THP of this invention can be used to produce transgenic animals, including fish that can withstand sub-zero temperatures. While some polar fish do synthesize antifreeze proteins, most fish do not live in environments where the water temperature drops below 0° C. However, transgenic fish containing exogenous nucleic acid encoding THP could be held and perhaps partially raised in sub-zero salt-water. In particular, salt-water fish being raised in farms, most particularly salmon. In addition to salmon, farmed transgenic prawns are a potential recipient of THP genes.

In addition to the above embodiments, it is envisioned that the THP of this invention can be used to regulate the expression of endogenous THP genes within a cold-tolerant organism. The expression of antifreeze protein gene products may be increased as a method of preparing, e.g., for subsequent isolation, endogenous antifreeze proteins. Conversely, by downregulating endogenous antifreeze gene expression, an otherwise cold-tolerant pest may be converted to a less aggravating phenotype.

Methods of altering the expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of one or more of the THP are altered.

This is typically accomplished by the use of homologous recombination to introduce a heterologous nucleic acid into the native regulatory sequences. To downregulate expression of one or more THP gene products, simple mutations that either alter the reading frame or disrupt the promoter are suitable. To upregulate expression of the THP gene products, the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs. Utilizing the structural gene sequence information provided in SEQ ID NOs:2 and 5 or the upstream or downstream sequence information provided in SEQ ID NO:s: 10, 12, 14 and 16, one of skill in the art can create homologous recombination constructs with only routine experimentation.

The use of homologous recombination to alter expression of endogenous genes is described in detail in U.S. Pat. No. 5,272,071, WO 91/09955, WO 93/09222, WO 96/29411, WO 95/31560, and WO 91/12650. Homologous recombination in mycobacteria is described by Azad, et al., *Proc. Nat'l Acad. Sci. USA* 93:4787 (1996); Baulard, et al., *J. Bacteriol.* 178:3091 (1996); and Pelicic, et al. *Mol. Microbiol.* 20:919 (1996). Homologous recombination in animals has been described by Moynahan, et al., in *Hum. Mol. Genet.* 5(7):875 (1996) and in plants by Offringa, et al. *EMBO J.* 9(10):3077 (1990).

Another embodiment is the introduction of an antifreeze protein into aqueous liquids surrounding an organ, tissue or other biological sample. One particular use would be during transportation to a hospital for a transplantation operation or for storage purposes. The antifreeze protein should allow short- or long-term storage at a subfreezing temperature, thereby minimizing inherent metabolism or degradation, but with substantially diminished cellular damage from ice crystal growth. Other medically important temperature sensitive biological samples are blood and blood products, therapeutic agents, protein drugs, bioassay reagents and vaccines.

Yet another embodiment is the introduction of an antifreeze protein into cells or their extracts destined for frozen storage. For example, bacterial cells, yeast cells, plant cells and, most particularly, animal cells containing the THP have increased cell or tissue viability with minimal or no loss of inherent characteristics due to the freeze-thaw process. Subcellular samples or cellular extracts may have similar sensitivities to freezing, especially on prolonged storage. Typical examples will be in vitro protein translation systems, enzyme preparations, and particularly samples which contain sensitive membrane components, such as chloroplast or mitochondrial membrane preparations. In particular, samples containing organelles may display increased resistance to freezing damage upon addition of these antifreeze polypeptides. Soft animal tissues will exhibit less damage upon freezing in the presence of the subject polypeptides, and addition of the polypeptides will be useful in situations when cellular integrity upon freezing and subsequent thawing is important or desired, such as for tissue culture deposits. Thus, samples destined for frozen storage, such as for cell or tissue depositories, might routinely have the proteins added to them. Among the cell types often stored are genetic variants of bacteria, fungi (including yeast), and, particularly, higher eukaryote cells (such as hybridoma strains and tissue culture cell lines).

Also included in the invention are compositions and uses based on the mixture of THP with stabilizers well known to those skilled in the art and other additives. These compounds may be present to inhibit decay, inhibit oxidation, prevent discoloration, inhibit microbial growth, stabilize emulsions and so forth.

Also included in the invention are compositions based on THPs suitable for depressing the freezing point or inhibiting freezing in non-organic systems, such as for use in deicing treatments.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

THP from *Tenebrio molitor* Larvae

The following example details the isolation of THP from the hemolymph of *Tenebrio molitor*. *Tenebrio molitor* larvae were reared as previously described (see, Graham, et al., *Insect Biochem. Molec. Biol.* 26:127 (1996)) but in darkness. Hemolymph (600 µL) was obtained from exudates at severed prolegs of 100 presumed final instar larvae and diluted 1:1 in ice-cold hemolymph buffer (50 mM Tris-HCl (pH 8.0), 150 mM NaCl and 1 mM phenylthiocarbamide.

Diluted hemolymph (1.2 mL) was loaded onto an S-100 SEPHACRYL® (Pharmacia) column (92 cm×1.6 cm) and eluted with hemolymph buffer without phenylthiocarbamide. Selected active fractions were combined and chromatographed by reversed-phase HPLC on a C18 analytical column (Vidac), using a gradient of 0.4% acetonitrile/min in 0.05% trifluoroacetic acid. Fractions were lyophilized and resuspended in 50 µL of 0.1 M $NH_4HCO_3$ (pH 8.0) for TH measurements following standard procedures (see, Chakrabarrty & Hew, *Eur. J. Biochem.* 202:1057 (1991)). Ice crystal morphology was photographed using black and white film, and crystal c and a axes were identified using cross-polarized light (Hobbs, ICE PHYSICS, Clarendon Press, London (1974)). Active fractions were resolved by 15% SDS-PAGE and stained using the Silver Stain Plus Kit (Bio-Rad).

Approximate molecular weights were determined by MALDI mass spectrometry. Two active, well-resolved HPLC fractions were subjected to amino acid analysis, N-terminal sequencing and electrospray ionization mass spectrometry. One fraction was reduced, alkylated, and cut with endoprotease Lys-C. Following separation of the cleavage products by reversed-phase HPLC, the best-resolved fragment was sequenced by automated Edman degradation.

Figure 2:
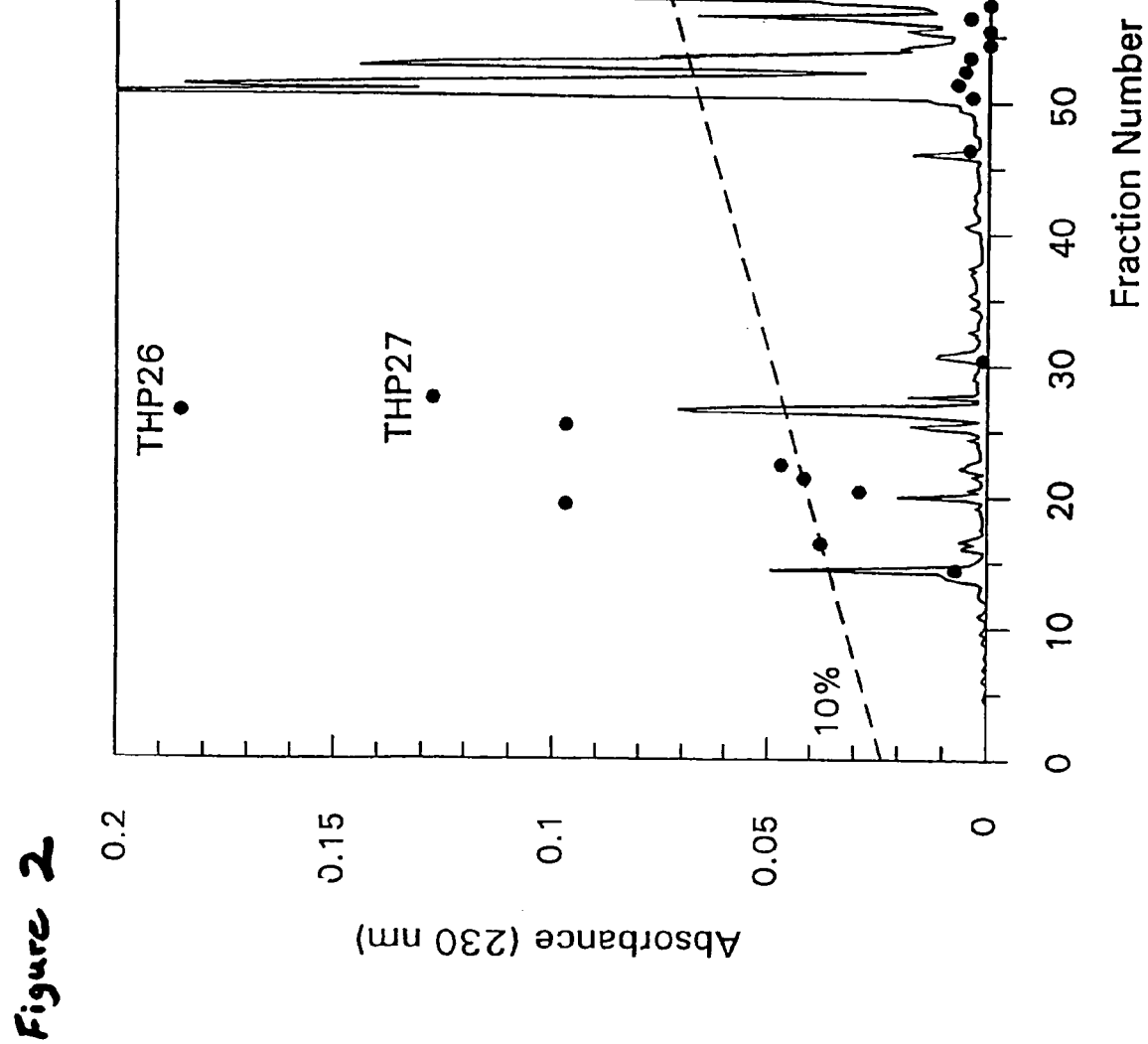
FIG. 2 is a chromatogram of selected active fractions from gel exclusion chromatography which were combined and chromatographed by reversed-phase HPLC on a C18 analytical column (Vidac), using a gradient of 0.4% acetonitrile/min in 0.05% trifluoroacetic acid.
Figure 3:
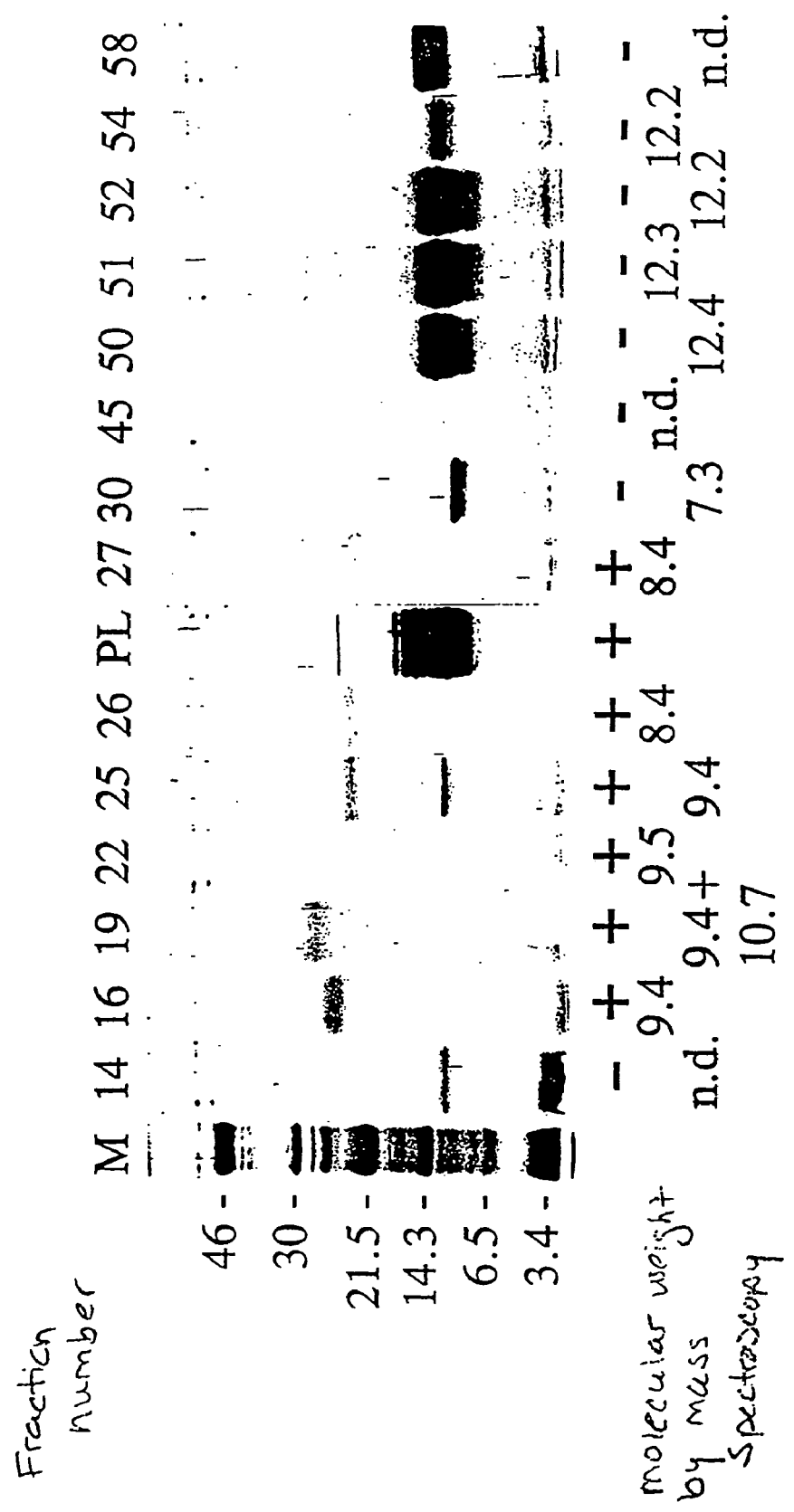
FIG. 3 is a 15% SDS-PAGE of reverse-phase HPLC fractions which were lyophilized and resuspended in 50 μL of 0.1 M $NH_4HCO_3$ (pH 8.0). The gel was stained using the Silver Stain Plus Kit (Bio-Rad). Approximate molecular weights were determined by MALDI mass spectrometry.

When diluted larval *Tenebrio* hemolymph was fractionated by gel exclusion chromatography, there were two overlapping peaks of TH activity with apparent molecular weights of approximately 19 and 17 kD (FIG. 1). When the leading peak was analyzed by HPLC, active proteins eluted between 16% and 22% acetonitrile (FIG. 2) and the more abundant but inactive proteins eluted later in the gradient. Mass spectrometry (FIG. 3) indicated that the inactive proteins (12.2 kDa to 12.4 kDa) migrated on SDS-PAGE according to their molecular mass, while the smaller TH proteins (7.3 kDa to 10.7 kDa) migrated anomalously as diffuse bands with apparent molecular weights ranging from 22 to 30 kDa. Fractions with the highest TH activity, corresponding to HPLC fractions 26 and 27 (FIG. 2), were analyzed for their amino acid content. The compositions of the two fractions were similar and both were rich in Thr and other amino acids with short side chains (Gly, Ala, Ser). Overall, the proteins were moderately hydrophilic (Wishard, et al., *Comput. Appl. Biosci.* 10:121 (1994)). The TH activities of THP26 (fraction 26) at 55 µg/mL and of THP27 at 21 µg/mL were 1.6° C. and 1.1° C., respectively, close to the maximum values obtained with 10-30 mg/mL of fish AFPs (Davies & Hew, *FASEB J.* 4:2460 (1990)).

Both THP26 and THP27 were N-terminally blocked. An internal fragment from THP26 released by endoproteinase Lys-C digestion was sequenced, and its amino acid content, including 7 Thr out of 20 residues, was consistent with the overall amino acid composition. Degenerate primers to this sequence were used in conjunction with vector primers to generate PCR products for screening a *Tenebrio* cDNA library.

Example 2 cDNA Library Screening for THP-Encoding Genes

To isolate other isoforms of tile THP of this invention, oligonucleotides for probes (SEQ ID NOs:2 and 5), PCR primers (SEQ ID NOs: 6 and 7) and sequencing primers (SEQ ID NOs: 8 and 9) were designed based on the consensus sequence determined from sequencing TH positive clones (YL-1-4).

Aliquots of a *Tenebrio molitor* larval fat body λ-Zap cDNA library (see, Graham, et al. *Insect Biochem. Molec. Biol.* 26:127 (1996)) were screened with the nucleic acid sequence of YL-1 from the 5' end to the stop codon SEQ ID NO:21). Approximately 1×10$^5$ plaques were screened at moderate stringency following standard methodologies using the sequence listed above. Isolated positive plaques were subjected to in vivo excision using R408 helper phage (Stratagene) as per manufacturer's instructions. The double-stranded DNA obtained was purified and sequenced as above using the vector primers T7 and T3 as well as SEQ ID NOs: 8 and 9.

The conceptual translations from the nucleic acid sequencing matched the sequenced peptide fragment at up to 18 of the 20 residues. The first 28 amino acids represented a secretory signal peptide with Cys at the −3 and −1 positions (von Heijne, *Nucl. Acids Res.* 14:4683 (1986)). The N-terminal amino acid of three of the variants was predicted to be Gln. This was consistent with N-terminal blockage in which the N-terminal Gln was converted to pyroglutamate by cyclization. The cleavage site of the fourth variant was not clearly predicted.

Example 3

Subcloning and Protein Expression

PCR linker-primers (SEQ ID NO: 6 and 7) were designed to amplify the THP coding region and to introduce a Met codon before the presumed N-terminal residue of the mature protein. The resulting fragment was ligated into the pET-20b (+) vector (Novagen) and transformed into *E. coli* BL21 (DE3). Expression was induced using isopropyl β-D-thiogalactopyranoside, cells were harvested by centrifugation, and sonicated in 10 mM Tris-HCl (pH8.0), 1 mM EDTA, 0.1 mM phenylmethylsulfonyl fluoride. Cleared supernatant was loaded onto a G75 gel exclusion chromatography column. Active fractions were pooled, lyophilized, resuspended in 50 mM Tris-HCl (pH 8.0), and dialyzed overnight against the same buffer.

Example 4

Functional Activity from Cloned THP

Figure 4:
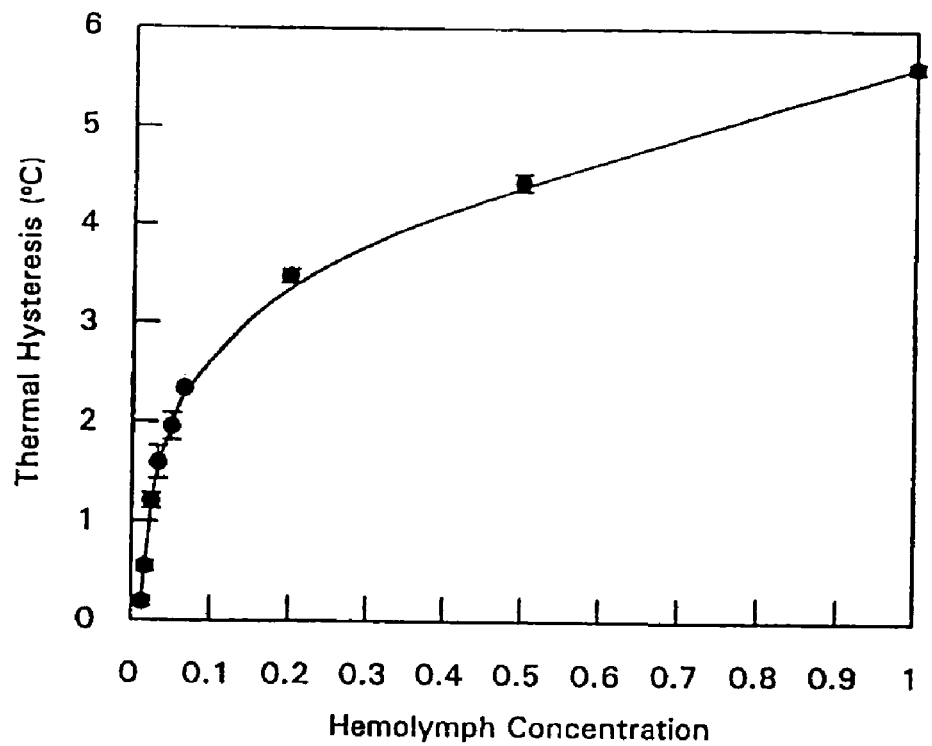
FIG. 4 is a graph indicating the hyperbolic nature of the thermal hysteresis activity of *Tenebrio* hemolymph.
Figure 5:
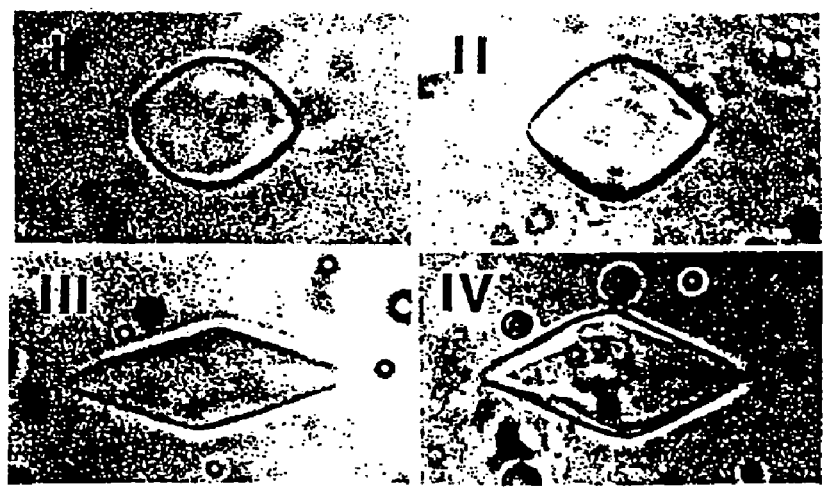
FIGS. 5 I-IV, are micro-photographs of ice crystals grown in the presence of *Tenebrio* THP (I and II) and fish antifreeze proteins (III and IV).

To prove that the cloned sequence codes for a THP, the shortest of the four cDNAs with a conventional signal cleavage site (YL-2, FIG. 6) was expressed in *E. coli*. TH activity was detected in the supernate of the cell lysate, indicating that some of the protein was able to fold well enough to display activity. Partially purified recombinant THP showed 5.3° C. of TH and was indistinguishable in its properties from the THP in *Tenebrio* hemolymph. Its activity was eliminated by reduction but was unaffected by chelation. Also, ice crystals formed in the presence of dilute hemilolymph (FIG. 4-I) and recombinant protein were identical (FIGS. 4-II). These observations suggest that this THP and its isoforms can account for all the TH activity in the insect. Moreover, extensive analysis of hemolymph and total extracts have shown no evidence of THP that are unrelated to these isoforms.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
        (A) LENGTH: 12 amino acids

```
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..12
        (D) OTHER INFORMATION: /note= "consensus 12 amino acid
            repeating motif"

(xi) SEQUENCE DESCRIPTION: SEQ ID NO: 1:

Cys Thr Xaa Ser Xaa Xaa Cys Xaa Xaa Ala Xaa Thr
1               5                   10

(2) INFORMATION FOR SEQ ID NO: 2:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..68
        (D) OTHER INFORMATION: /note= "conserved N-terminal region of
            thermal hysteresis protein (THP)
            isoforms"

(xi) SEQUENCE DESCRIPTION: SEQ ID NO: 2:

TGCACTGGGG STGCTGATTG YACTAGTTGT ACAGVWGCAT GCACTGGTTG TGGAARYTGT      60

CCAAATGC                                                              68

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "consensus 16 amino acid
            N-terminal motif for YL-1, YL-2, YL-3
            and YL-4"

(xi) SEQUENCE DESCRIPTION: SEQ ID NO: 3:

Xaa Cys Thr Xaa Xaa Xaa Xaa Cys Thr Xaa Cys Thr Xaa Xaa Cys Thr
1               5                   10                  15

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..24
        (D) OTHER INFORMATION: /note= "N-terminal amino acid sequence
``` of YL-1, YL-2, YL-3 and YL-4"

(ix) FEATURE:
             (A) NAME/KEY: Modified-site
             (B) LOCATION: 1
             (D) OTHER INFORMATION: /product= "OTHER"
                 /note= "Xaa = Gln or His"

(ix) FEATURE:
             (A) NAME/KEY: Modified-site
             (B) LOCATION: 5
             (D) OTHER INFORMATION: /product= "OTHER"
                 /note= "Xaa = Ala or Gly"

(ix) FEATURE:
             (A) NAME/KEY: Modified-site
             (B) LOCATION: 13
             (D) OTHER INFORMATION: /product= "OTHER"
                 /note= "Xaa = Ala, Asp or Gly"

(ix) FEATURE:
             (A) NAME/KEY: Modified-site
             (B) LOCATION: 20
             (D) OTHER INFORMATION: /product= "OTHER"
                 /note= "Xaa = Asn or Ser"

(xi) SEQUENCE DESCRIPTION: SEQ ID NO: 4:

Xaa Cys Thr Gly Xaa Ala Asp Cys Thr Ser Cys Thr Xaa Ala Cys Thr
1               5                   10                  15

Gly Cys Gly Xaa Cys Pro Asn Ala
            20

(2) INFORMATION FOR SEQ ID NO: 5:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..61
         (D) OTHER INFORMATION: /note= "conserved C-terminal region of
             thermal hysteresis protein (THP)
             isoforms"

(xi) SEQUENCE DESCRIPTION: SEQ ID NO: 5:

CTCAACCAAC TGTTACAAAG CTACAGCCTG TACCAATTCA WCAGGATGTC CCGGACATTA     60

R                                                                    61

(2) INFORMATION FOR SEQ ID NO: 6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..32
         (D) OTHER INFORMATION: /note= "PCR primer"

(xi) SEQUENCE DESCRIPTION: SEQ ID NO: 6:

CATATGCATA TGCAATGCAC TGGGGGTGCT GA                                  32

-continued (2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..32
        (D) OTHER INFORMATION: /note= "PCR primer"

(xi) SEQUENCE DESCRIPTION: SEQ ID NO: 7:

AAGCCTAAGC TTTTAATGTC CGGGACATCC TG                                           32

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "internal downstream facing
            sequencing primer"

(xi) SEQUENCE DESCRIPTION: SEQ ID NO: 8:

AAAGACTGTT TTGAAGCC                                                            18

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "internal upstream facing
            sequencing primer"

(xi) SEQUENCE DESCRIPTION: SEQ ID NO: 9:

TTCAAAACAG TCTTTTGA                                                            18

(2) INFORMATION FOR SEQ ID NO: 10:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..559
        (D) OTHER INFORMATION: /note= "YL-1 thermal hysteresis protein
        (THP) cDNA from Tenebrio molitor"

(ix) FEATURE:

(A) NAME/KEY: CDS
            (B) LOCATION: 37..375
            (D) OTHER INFORMATION: /product= "YL-1"

(xi) SEQUENCE DESCRIPTION: SEQ ID NO: 10:

TAAACAGCGA GATAAACAAC AATACTACAT AAAACT ATG GCG TTC AAA ACG TGT      54
                                        Met Ala Phe Lys Thr Cys
                                        1               5

GGT TTT TCA AAA AAA TGG TTA GTA ATA GCA GTT ATA GTT ATG TGT TTG     102
Gly Phe Ser Lys Lys Trp Leu Val Ile Ala Val Ile Val Met Cys Leu
            10                  15                  20

TGT ACC GAG TGT TAT TGC CAC TGC ACT GGG GGT GCT GAT TGT ACT AGT     150
Cys Thr Glu Cys Tyr Cys His Cys Thr Gly Gly Ala Asp Cys Thr Ser
            25                  30                  35

TGT ACA GAT GCA TGC ACT GGT TGT GGA AAT TGT CCA AAT GCA CAT ACG     198
Cys Thr Asp Ala Cys Thr Gly Cys Gly Asn Cys Pro Asn Ala His Thr
        40                  45                  50

TGT ACC GAT TCC AAA AAT TGT GTC AAG GCA GCA ACA TGT ACT GGA TCT     246
Cys Thr Asp Ser Lys Asn Cys Val Lys Ala Ala Thr Cys Thr Gly Ser
    55                  60                  65                  70

ACA AAA TGT AAT ACC GCC AGG ACG TGT ACA AAC TCA AAA GAC TGT TTT     294
Thr Lys Cys Asn Thr Ala Arg Thr Cys Thr Asn Ser Lys Asp Cys Phe
            75                  80                  85

GAA GCC AAA ACA TGT ACT GAC TCA ACC AAC TGT TAC AAA GCT ACA GCC     342
Glu Ala Lys Thr Cys Thr Asp Ser Thr Asn Cys Tyr Lys Ala Thr Ala
            90                  95                  100

TGT ACC AAT TCA ACA GGA TGT CCC GGA CAT TAAGTTTTTC TATTGTCAAC       392
Cys Thr Asn Ser Thr Gly Cys Pro Gly His
            105                 110

AATAATAAAA CACACTTACT GTTATCTTAG CTAAAACATA ATTGTAAGCT CACTCTGTTT   452

TGTATCCTAT CTGTCTCTGC CTCCGAAGGA TGATAATTTT GTACTGGGAG CGAAAGGTTT   512

ATCCGACAAT AATAAACTAA AATAATTGAT ATAAAAAAAA AAAAAA                  559

(2) INFORMATION FOR SEQ ID NO: 11:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 11:

Met Ala Phe Lys Thr Cys Gly Phe Ser Lys Lys Trp Leu Val Ile Ala
1               5                   10                  15

Val Ile Val Met Cys Leu Cys Thr Glu Cys Tyr Cys His Cys Thr Gly
            20                  25                  30

Gly Ala Asp Cys Thr Ser Cys Thr Asp Ala Cys Thr Gly Cys Gly Asn
        35                  40                  45

Cys Pro Asn Ala His Thr Cys Thr Asp Ser Lys Asn Cys Val Lys Ala
    50                  55                  60

Ala Thr Cys Thr Gly Ser Thr Lys Cys Asn Thr Ala Arg Thr Cys Thr
65                  70                  75                  80

Asn Ser Lys Asp Cys Phe Glu Ala Lys Thr Cys Thr Asp Ser Thr Asn
            85                  90                  95

Cys Tyr Lys Ala Thr Ala Cys Thr Asn Ser Thr Gly Cys Pro Gly His
            100                 105                 110

(2) INFORMATION FOR SEQ ID NO: 12:

(i) SEQUENCE CHARACTERISTICS:
    (A) LENGTH: 529 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: -
    (B) LOCATION: 1..529
    (D) OTHER INFORMATION: /note= "YL-2 thermal hysteresis protein
    (THP) cDNA from Tenebrio molitor"

(ix) FEATURE:
    (A) NAME/KEY: CDS
    (B) LOCATION: 21..359
    (D) OTHER INFORMATION: /product= "YL-2"

(xi) SEQUENCE DESCRIPTION: SEQ ID NO: 12:

```
AAACAATATT ACAAAAAACT ATG GCA TTC AAA ACG TGT GGT TTT TCA AAA            50
                     Met Ala Phe Lys Thr Cys Gly Phe Ser Lys
                     1               5                  10

AAA TGG TTA GTA ATA GCA GTT ATA GTT ATG TGT TTG TGT ACC GAG TGT          98
Lys Trp Leu Val Ile Ala Val Ile Val Met Cys Leu Cys Thr Glu Cys
             15                  20                  25

TAT TGC CAA TGC ACT GGG GGT GCT GAT TGC ACT AGT TGT ACA GGA GCA         146
Tyr Cys Gln Cys Thr Gly Gly Ala Asp Cys Thr Ser Cys Thr Gly Ala
             30                  35                  40

TGC ACT GGT TGT GGA AAC TGT CCA AAT GCA GTA ACG TGT ACC AAT TCT         194
Cys Thr Gly Cys Gly Asn Cys Pro Asn Ala Val Thr Cys Thr Asn Ser
         45                  50                  55

CAA CAT TGT GTC AAG GCA AAT ACA TGT ACT GGG TCT ACA GAT TGT AAT         242
Gln His Cys Val Lys Ala Asn Thr Cys Thr Gly Ser Thr Asp Cys Asn
     60                  65                  70

ACA GCC CAG ACG TGT ACA AAC TCA AAA GAC TGT TTT GAA GCC AAC ACA         290
Thr Ala Gln Thr Cys Thr Asn Ser Lys Asp Cys Phe Glu Ala Asn Thr
 75                  80                  85                  90

TGT ACT GAC TCA ACC AAC TGT TAC AAA GCT ACA GCC TGT ACC AAT TCA         338
Cys Thr Asp Ser Thr Asn Cys Tyr Lys Ala Thr Ala Cys Thr Asn Ser
                 95                 100                 105

TCA GGA TGT CCC GGA CAT TAAGTTTTTC TATTGTCAAC AATCATAAAA                386
Ser Gly Cys Pro Gly His
             110

CACAATTATT GTTAGCTAAG TTAAAACTCT GTATTGTATC CGATCTGTCT CTTTGCCTCC       446

CAAGGATGAT AATTTTGTAC TGGGAGCGAA AGGGTTATCG GACAATAATA AACTAAAATA       506

ATTGATATAA AAAAAAAAA AAA                                                529
```

(2) INFORMATION FOR SEQ ID NO: 13:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Ala Phe Lys Thr Cys Gly Phe Ser Lys Lys Trp Leu Val Ile Ala
1               5                  10                  15

Val Ile Val Met Cys Leu Cys Thr Glu Cys Tyr Cys Gln Cys Thr Gly
            20                  25                  30

Gly Ala Asp Cys Thr Ser Cys Thr Gly Ala Cys Thr Gly Cys Gly Asn
```

-continued

```
                        35                  40                  45
        Cys Pro Asn Ala Val Thr Cys Thr Asn Ser Gln His Cys Val Lys Ala
             50                  55                  60

Asn Thr Cys Thr Gly Ser Thr Asp Cys Asn Thr Ala Gln Thr Cys Thr
         65                  70                  75                  80

Asn Ser Lys Asp Cys Phe Glu Ala Asn Thr Cys Thr Asp Ser Thr Asn
                         85                  90                  95

Cys Tyr Lys Ala Thr Ala Cys Thr Asn Ser Ser Gly Cys Pro Gly His
                    100                 105                 110
```

(2) INFORMATION FOR SEQ ID NO: 14:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..642
        (D) OTHER INFORMATION: /note= "YL-4 thermal hysteresis protein
        (THP) cDNA from Tenebrio molitor"

(ix) FEATURE:
        (A) NAME/KEY: CDS
        (B) LOCATION: 10..456
        (D) OTHER INFORMATION: /product= "YL-4"

(xi) SEQUENCE DESCRIPTION: SEQ ID NO: 14:

```
CAAAAAAGT ATG TCA TTC AAA ATA AGT ACT TTT ACA AAA ATC TGG TTA              48
          Met Ser Phe Lys Ile Ser Thr Phe Thr Lys Ile Trp Leu
           1               5                  10

ATT ATA GCA GTT ATC GTT ATG TGT TTG TGT AAC GAG TAT AAT TGC CAG            96
Ile Ile Ala Val Ile Val Met Cys Leu Cys Asn Glu Tyr Asn Cys Gln
         15                  20                  25

TGC ACT GGG GCT GCT GAT TGT ACT AGT TGT ACA GCA GCA TGC ACT GGT           144
Cys Thr Gly Ala Ala Asp Cys Thr Ser Cys Thr Ala Ala Cys Thr Gly
 30                  35                  40                  45

TGT GGA AAC TGT CCA AAT GCA ATA ACG TGT ACC GGT TCT AAA AAT TGT           192
Cys Gly Asn Cys Pro Asn Ala Ile Thr Cys Thr Gly Ser Lys Asn Cys
                 50                  55                  60

GTC AGG GCA ACA ACA TGT ACT GGG TCT ACA AAC TGT AAT AGA GCC ACG           240
Val Arg Ala Thr Thr Cys Thr Gly Ser Thr Asn Cys Asn Arg Ala Thr
                 65                  70                  75

ACG TGT ACA AAT TCA AAA GGC TGT TTA GAA GCC ACA ACA TGT ACT GGG           288
Thr Cys Thr Asn Ser Lys Gly Cys Leu Glu Ala Thr Thr Cys Thr Gly
             80                  85                  90

TCT ACA CAC TGT CAT AGA GCC ACG ACG TGT ACA AAT TCA AAA GAC TGT           336
Ser Thr His Cys His Arg Ala Thr Thr Cys Thr Asn Ser Lys Asp Cys
     95                 100                 105

TTT GAA GCC ACA ACA TGT ACT GGC TCA AGC AAC TGT TAC ACT GCT ACA           384
Phe Glu Ala Thr Thr Cys Thr Gly Ser Ser Asn Cys Tyr Thr Ala Thr
110                 115                 120                 125

ACA TGT ACT AAC TCA ACC AAC TGT TAC AAA GCT ACA GCC TGT ACC AAT           432
Thr Cys Thr Asn Ser Thr Asn Cys Tyr Lys Ala Thr Ala Cys Thr Asn
                130                 135                 140

TCA ACA GGA TGT CCC GGA CAT TAGGTTTTTT TATTGTCAAC AATAAAATAA              483
Ser Thr Gly Cys Pro Gly His
            145

AACAAAACTG TTCTTATCTA AGCTAAAACA TAAATGTAAA CGTTAATTTG TATTCTATCC         543
```

```
GATCTGTCCC TTTGCGCCCT AAGGATAATT TTGTACAGGG AGAGAAAAGG CTATCGGACA        603

ATAATAAACA TTGTTAATAT ACATAAAAAA AAAAAAAA                                642

(2) INFORMATION FOR SEQ ID NO: 15:

(i) SEQUENCE CHARACTERISTICS:
        (A) LENGTH: 148 amino acids
        (B) TYPE: amino acid
        (D) TOPOLOGY: linear (ii) MOLECULE TYPE: protein (xi) SEQUENCE DESCRIPTION: SEQ ID NO: 15:

Met Ser Phe Lys Ile Ser Thr Phe Thr Lys Ile Trp Leu Ile Ile Ala
1               5                   10                  15

Val Ile Val Met Cys Leu Cys Asn Glu Tyr Asn Cys Gln Cys Thr Gly
                20                  25                  30

Ala Ala Asp Cys Thr Ser Cys Thr Ala Ala Cys Thr Gly Cys Gly Asn
            35                  40                  45

Cys Pro Asn Ala Ile Thr Cys Thr Gly Ser Lys Asn Cys Val Arg Ala
        50                  55                  60

Thr Thr Cys Thr Gly Ser Thr Asn Cys Asn Arg Ala Thr Thr Cys Thr
65                  70                  75                  80

Asn Ser Lys Gly Cys Leu Glu Ala Thr Thr Cys Thr Gly Ser Thr His
                85                  90                  95

Cys His Arg Ala Thr Thr Cys Thr Asn Ser Lys Asp Cys Phe Glu Ala
                100                 105                 110

Thr Thr Cys Thr Gly Ser Ser Asn Cys Tyr Thr Ala Thr Thr Cys Thr
            115                 120                 125

Asn Ser Thr Asn Cys Tyr Lys Ala Thr Ala Cys Thr Asn Ser Thr Gly
        130                 135                 140

Cys Pro Gly His
145

(2) INFORMATION FOR SEQ ID NO: 16:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..587
        (D) OTHER INFORMATION: /note= "YL-3 thermal hysteresis protein
        (THP) cDNA from Tenebrio molitor"

(ix) FEATURE:
        (A) NAME/KEY: CDS
        (B) LOCATION: 24..398
        (D) OTHER INFORMATION: /product= "YL-3"

(xi) SEQUENCE DESCRIPTION: SEQ ID NO: 16:

AAACAACAAT ATTACAAAAA ACT ATG GCA TTC AAA ACG TGT GGT TTT TCA            50
                        Met Ala Phe Lys Thr Cys Gly Phe Ser
                         1               5

AAA AAA TGG TTA ATA ATA GCA GTT ATA GTT ATG TGT TTG TGT ACC GAG          98
Lys Lys Trp Leu Ile Ile Ala Val Ile Val Met Cys Leu Cys Thr Glu
 10              15                  20                  25
```

```
TGT TAT TGC CAA TGC ACT GGG GGT GCT GAT TGT ACT AGT TGT ACA GCA      146
Cys Tyr Cys Gln Cys Thr Gly Gly Ala Asp Cys Thr Ser Cys Thr Ala
             30                  35                  40

GCA TGC ACT GGT TGT GGA AGT TGT CCA AAT GCG CAT ACG TGT ACC GAT      194
Ala Cys Thr Gly Cys Gly Ser Cys Pro Asn Ala His Thr Cys Thr Asp
                 45                  50                  55

TCT AAA AAT TGT GTC AGG GCA GAA ACG TGT ACC GAT TCT GAA AAT TGT      242
Ser Lys Asn Cys Val Arg Ala Glu Thr Cys Thr Asp Ser Glu Asn Cys
             60                  65                  70

GTC AAG GCA CAT ACA TGT ACT GGA TCT AGA AAC TGT AAT ACA GCC ATG      290
Val Lys Ala His Thr Cys Thr Gly Ser Arg Asn Cys Asn Thr Ala Met
 75                  80                  85

ACG TGT ACA AAC TCA AAA GAC TGT TTT GAA GCC AAA ACA TGT ACT GAC      338
Thr Cys Thr Asn Ser Lys Asp Cys Phe Glu Ala Lys Thr Cys Thr Asp
 90                  95                 100                 105

TCA ACC AAC TGT TAC AAA GCT ACA GCC TGT ACC AAT TCA ACA GGA TGT      386
Ser Thr Asn Cys Tyr Lys Ala Thr Ala Cys Thr Asn Ser Thr Gly Cys
                110                 115                 120

CCC GGA CAT TAAGTTTTTC TATTGTCAAC AATAATAAAA CACGGAGGGA              435
Pro Gly His

TAGTCTAAGC TAAAACATAA TTGTAAGCTT ACTCTGTATT GTATCCGATC TGTCTCTTTG    495

CCTCCCAAGG ATGATAATTT TGTACTGGGA GCGAAAGGGT TACCGGACAA TAATAATTAA    555

TAAACTAAAT AATTGATAAA AAAAAAAAAA AA                                  587

(2) INFORMATION FOR SEQ ID NO: 17:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 17:

Met Ala Phe Lys Thr Cys Gly Phe Ser Lys Lys Trp Leu Ile Ile Ala
 1               5                  10                  15

Val Ile Val Met Cys Leu Cys Thr Glu Cys Tyr Cys Gln Cys Thr Gly
                20                  25                  30

Gly Ala Asp Cys Thr Ser Cys Thr Ala Ala Cys Thr Gly Cys Gly Ser
             35                  40                  45

Cys Pro Asn Ala His Thr Cys Thr Asp Ser Lys Asn Cys Val Arg Ala
         50                  55                  60

Glu Thr Cys Thr Asp Ser Glu Asn Cys Val Lys Ala His Thr Cys Thr
 65                  70                  75                  80

Gly Ser Arg Asn Cys Asn Thr Ala Met Thr Cys Thr Asn Ser Lys Asp
                 85                  90                  95

Cys Phe Glu Ala Lys Thr Cys Thr Asp Ser Thr Asn Cys Tyr Lys Ala
                100                 105                 110

Thr Ala Cys Thr Asn Ser Thr Gly Cys Pro Gly His
            115                 120

(2) INFORMATION FOR SEQ ID NO: 18:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: cDNA
```

(ix) FEATURE:
    (A) NAME/KEY: -
    (B) LOCATION: 1..602
    (D) OTHER INFORMATION: /note= "5-15 cDNA"

(ix) FEATURE:
    (A) NAME/KEY: CDS
    (B) LOCATION: 36..410
    (D) OTHER INFORMATION: /product= "5-15"

(xi) SEQUENCE DESCRIPTION: SEQ ID NO: 18:

```
AAACAGCGAG ATAAACAACA ATATTACAAA AAACT ATG GCA TTC AAA ACG TGT        53
                                       Met Ala Phe Lys Thr Cys
                                         1               5

GGT TTT TCA AAA AAA TGG TTA ATA ATA GCA GTT ATA GTT ATG TGT TTG       101
Gly Phe Ser Lys Lys Trp Leu Ile Ile Ala Val Ile Val Met Cys Leu
            10                  15                  20

TGT ACC GAG TGT TAT TGC CAA TGC ACT GGG GGT GCT GAT TGT ACT AGT       149
Cys Thr Glu Cys Tyr Cys Gln Cys Thr Gly Gly Ala Asp Cys Thr Ser
        25                  30                  35

TGT ACA GCA GCA TGC ACT GGT TGT GGA AGT TGT CCA AAT GCG CAT ACG       197
Cys Thr Ala Ala Cys Thr Gly Cys Gly Ser Cys Pro Asn Ala His Thr
    40                  45                  50

TGT ATC GAT TCT AAA AAT TGT GTC AGG GCA GAA ACG TGT ACC GAT TCT       245
Cys Ile Asp Ser Lys Asn Cys Val Arg Ala Glu Thr Cys Thr Asp Ser
55                  60                  65                  70

GAA AAT TGT GTC AAG GCA CAT ACA TGT ACT GGA TCT AGA AAC TGT AAT       293
Glu Asn Cys Val Lys Ala His Thr Cys Thr Gly Ser Arg Asn Cys Asn
                75                  80                  85

ACA GCC ATG ACG TGT ACA AAC TCA AAA GAC TGT TTT GAA GCC AAA ACA       341
Thr Ala Met Thr Cys Thr Asn Ser Lys Asp Cys Phe Glu Ala Lys Thr
            90                  95                  100

TGT ACT GAC TCA ACC AAC TGT TAC AAA GCT ACA GCC TGT ACC AAT TCA       389
Cys Thr Asp Ser Thr Asn Cys Tyr Lys Ala Thr Ala Cys Thr Asn Ser
        105                 110                 115

ACA GGA TGT CCC GGA CAT TAAGTTTTTC TATTGTCAAC AATAATAAAA              437
Thr Gly Cys Pro Gly His
    120

CACGGAGGGA TAGTCTAAGC TAAAACATAA TTGTAAGCTT ACTCTGTATT GTATCCGATC     497

TGTCTCTTTG CCTCCCAAGG ATGATAATTT TGTACTGGGA GCGAAAGGGT TACCGGACAA     557

TAATAATTAA TAAACTAAAA TAATTGATAT AAAAAAAAAA AAAAA                     602
```

(2) INFORMATION FOR SEQ ID NO: 19:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 19:

```
Met Ala Phe Lys Thr Cys Gly Phe Ser Lys Lys Trp Leu Ile Ile Ala
  1               5                  10                  15

Val Ile Val Met Cys Leu Cys Thr Glu Cys Tyr Cys Gln Cys Thr Gly
             20                  25                  30

Gly Ala Asp Cys Thr Ser Cys Thr Ala Ala Cys Thr Gly Cys Gly Ser
         35                  40                  45

Cys Pro Asn Ala His Thr Cys Ile Asp Ser Lys Asn Cys Val Arg Ala
     50                  55                  60
```

```
Glu Thr Cys Thr Asp Ser Glu Asn Cys Val Lys Ala His Thr Cys Thr
 65                  70                  75                  80

Gly Ser Arg Asn Cys Asn Thr Ala Met Thr Cys Thr Asn Ser Lys Asp
                 85                  90                  95

Cys Phe Glu Ala Lys Thr Cys Thr Asp Ser Thr Asn Cys Tyr Lys Ala
            100                 105                 110

Thr Ala Cys Thr Asn Ser Thr Gly Cys Pro Gly His
        115                 120
```

(2) INFORMATION FOR SEQ ID NO: 20:

(i) SEQUENCE CHARACTERISTICS:
        (A) LENGTH: 555 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..555
        (D) OTHER INFORMATION: /note= "consensus thermal hysteresis
            protein (THP) cDNA"

(xi) SEQUENCE DESCRIPTION: SEQ ID NO: 20:

```
AAACAGCGAG ATAAANAACA ATANTACANA AAANTATGNC NTTCAAAANN NGTNNTTTTN     60

CAAAAANNTG GTTANTNATA GCAGTTATNG TTATGTGTTT GTGTANCGAG TNTNATTGCC    120

ANTGCACTGG GGNTGCTGAT TGNACTAGTT GTACAGNNGC ATGCACTGGT TGTGGAANNT    180

GTCCAAATGC NNNNACGTGT ANCNNTTCNN AANATTGTGT CANGGCANNN ACATGTACTG    240

GNTCTANANA NTGTAATANN GCCNNGACGT GTACAAANTC AAAAGNCTGT TTNGAAGCCA    300

NNACATGTAC TGACTCAACC AACTGTTACA AAGCTACAGC CTGTACCAAT TCANCAGGAT    360

GTCCCGGACA TTANGTTTTT NTATTGTCAA CAATNNNATA AAACANNNNN NNNNTNNNCT    420

NAGNTAAAAC NNNNNTGTAN NNNNNNNNNT GTNTNNNATC NNNNNTGTCN CTNNGCNNCC    480

NAAGGANNNT AATTTTGTAC NGGGAGNGAA ANGNNTANCN GACAATAATA NNNNNNNAAC    540

NNNNNTAATN NNNAT                                                    555
```

(2) INFORMATION FOR SEQ ID NO: 21:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..313
        (D) OTHER INFORMATION: /note= "Y1-1 nucleic acid probe used to
            screen Tenebrio molitor larval fat body
            lambda-Zap cDNA library"

(xi) SEQUENCE DESCRIPTION: SEQ ID NO: 21:

```
CACTGCACTG GGGGTGCTGA TTGTACTAGT TGTACAGATG CATGCACTGG TTGTGGAAAT     60

TGTCCAAATG CACATACGTG TACCGATTCC AAAAATTGTG TCAAGGCAGC AACATGTACT    120

GGATCTACAA AATGTAATAC CGCCAGGACG TGTACAAACT CAAAGACTG TTTTGAAGCC     180

AAAACATGTA CTGACTCAAC CAACTGTTAC AAAGCTACAG CCTGTACCAA TTCAACAGGA    240
```

```
                                                   -continued
TGTCCCGGAC ATTAAGTTTT TCTATTGTCA ACAATAATAA AACACACTTA CTGTTATCTT      300

AGCTAAAACA TAA                                                        313

(2) INFORMATION FOR SEQ ID NO: 22:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Cys Xaa Xaa Xaa Xaa Xaa Cys Xaa Xaa Cys Xaa Xaa Xaa Cys Xaa Xaa
 1               5                  10                  15

Cys Xaa Xaa Cys
            20
```

What is claimed is:

1. An isolated or recombinantly expressed antifreeze protein, said protein comprising the following:
   (i) a calculated molecular weight of between 7 and 13 kDa;
   (ii) a thermal hysteresis activity of greater than 1.5° C. at a concentration of about 1 mg/mL;
   (iii) the N-terminal amino acid motif set forth in SEQ ID NO:3;
   (iv) at least 70% amino acid sequence identity to the antifreeze protein of SEQ ID NO:15 (YL-4); and
   (v) at least 4 repeats of the 12 contiguous amino acid motif set forth in SEQ ID NO:1.

2. The isolated or recombinantly expressed antifreeze protein of claim 1 comprising at least 5 repeats of the 12 contiguous amino acid motif set forth in SEQ ID NO:1.

3. The isolated or recombinantly expressed antifreeze protein of claim 1 comprising 5 to 12 repeats of the 12 contiguous amino acid motif set forth in SEQ ID NO:1.

4. The isolated or recombinant antifreeze protein of claim 1, wherein the calculated molecular weight of the antifreeze protein is between 8 and 12 kDa.

5. The isolated or recombinant antifreeze protein of claim 1, wherein the antifreeze protein includes the subsequence of amino acids set forth in SEQ ID NO:4.

6. The isolated or recombinant antifreeze protein of claim 1, wherein the thermal hysteresis activity is greater than 2° C. at a concentration of about 1 mg/mL.

7. The isolated or recombinant antifreeze protein of claim 1, wherein the antifreeze protein is the polypeptide of SEQ ID NO:15 lacking its signal peptide.

8. The isolated or recombinant antifreeze protein of claim 1, wherein the antifreeze protein is expressed by a baculovirus vector.

9. The isolated or recombinant antifreeze protein of claim 1, wherein the antifreeze protein is synthesized by a bacterial cell, a fungus cell, a plant cell, or an animal cell.

10. The isolated or recombinant antifreeze protein of claim 1, wherein the antifreeze protein is synthesized by a yeast cell.

11. The isolated or recombinant antifreeze protein of claim 1, wherein the antifreeze protein is synthesized by an animal cell.

12. The isolated or recombinant antifreeze protein of claim 1, wherein the nucleic acid encoding the antifreeze protein is synthesized by an insect cell.

13. The isolated or recombinant antifreeze protein of claim 1, wherein the antifreeze protein is derived from *Tenebrio* sp.

14. The isolated or recombinant antifreeze protein of claim 9, wherein the antifreeze protein is expressed externally from the cell.

15. A liquid comprising a recombinant antifreeze protein, said antifreeze protein comprising the following:
   (i) a calculated molecular weight of between 7 and 13 kDa;
   (ii) a therminal hysteresis activity of greater than 1.5° C. at a concentration of about 1 mg/mL;
   (iii) the N-terminal amino acid motif set forth in SEQ ID NO:3;
   (iv) at least 70% amino acid sequence identity to the antifreeze protein of SEQ ID NO:15 (YL-4); and
   (v) at least 4 repeats of the 12 contiguous amino acid motif set forth in SEQ ID NO:1.

16. The liquid of claim 15 wherein said antifreeze protein comprises at least 5 repeats of the 12 contiguous amino acid motif set forth in SEQ ID NO:1.

17. The liquid of claim 15 wherein said antifreeze protein comprises 5 to 12 repeats of the 12 contiguous amino acid motif set forth in SEQ ID NO:1.

18. The liquid of claim 15, wherein the concentration of antifreeze protein is between about one part per billion (1 μg/L) to about one part per thousand (1 g/L).

19. The liquid of claim 15, wherein the antifreeze protein has a thermal hysteresis activity greater than 2° C. at a concentration of about 1 mg/mL.

* * * * *